(12) United States Patent
Monfre et al.

(10) Patent No.: US 7,697,966 B2
(45) Date of Patent: Apr. 13, 2010

(54) NONINVASIVE TARGETING SYSTEM METHOD AND APPARATUS

(75) Inventors: Stephen L. Monfre, Gilbert, AZ (US); Thomas B. Blank, Gilbert, AZ (US); Kevin H. Hazen, Gilbert, AZ (US); Alan Abul-Haj, Mesa, AZ (US); Tim Ruchti, Gilbert, AZ (US); James Ryan Henderson, Phoenix, AZ (US); Tim Stippick, Phoenix, AZ (US); Roxanne Abul-Haj, Mesa, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 1086 days.

(21) Appl. No.: 11/361,143

(22) Filed: Feb. 23, 2006

(65) Prior Publication Data

US 2006/0200017 A1 Sep. 7, 2006

Related U.S. Application Data

(60) Provisional application No. 60/656,727, filed on Feb. 25, 2005, provisional application No. 60/658,708, filed on Mar. 3, 2005, provisional application No. 60/658,821, filed on Mar. 4, 2005.

(51) Int. Cl.
*A61B 5/1455* (2006.01)
(52) U.S. Cl. .................................. 600/310; 600/316
(58) Field of Classification Search ................ 600/310, 600/322, 323
See application file for complete search history.

(56) References Cited

U.S. PATENT DOCUMENTS

| | | | |
|---|---|---|---|
| 4,033,054 A | 7/1977 | Fukuoka | |
| 4,213,462 A | 7/1980 | Sato | |
| 4,272,040 A | 6/1981 | Bastian et al. | |
| 4,321,930 A | 3/1982 | Jobsis | |
| 4,548,505 A | 10/1985 | Ono | |
| 4,674,338 A | 6/1987 | Carpenter | |
| 4,685,464 A | 8/1987 | Goldberger et al. | |
| 4,798,955 A | 1/1989 | Rosenthal | |
| 4,830,014 A | 5/1989 | Goodman et al. | |
| 4,866,644 A | 9/1989 | Shenk et al. | |
| 4,882,492 A | 11/1989 | Schlager | |
| 5,007,423 A | 4/1991 | Branstetter et al. | |

(Continued)

FOREIGN PATENT DOCUMENTS

CN 1214768 4/1999

(Continued)

OTHER PUBLICATIONS

Webster's II New Riverside University Dictionary: The Riverside Publishing Company, 1994, p. 1000.

(Continued)

*Primary Examiner*—Eric F Winakur
(74) *Attorney, Agent, or Firm*—Michael A. Glenn; Glenn Patent Group

(57) ABSTRACT

The invention provides a targeting system used to direct a measuring system to a targeted sample site or volume. The targeting system increases analyte estimation performance by increasing precision and accuracy of sampling and/or by targeting an analyte rich tissue volume.

22 Claims, 9 Drawing Sheets

U.S. PATENT DOCUMENTS

| | | | |
|---|---|---|---|
| 5,068,536 A | 11/1991 | Rosenthal | |
| 5,070,874 A | 12/1991 | Barnes et al. | |
| 5,131,391 A | 7/1992 | Sakai et al. | |
| 5,170,786 A | 12/1992 | Thomas | |
| 5,285,783 A | 2/1994 | Secker | |
| 5,299,570 A | 4/1994 | Hatschek | |
| 5,348,003 A | 9/1994 | Caro | |
| 5,361,758 A | 11/1994 | Hall et al. | |
| 5,398,681 A | 3/1995 | Kupershmidt | |
| 5,448,662 A | 9/1995 | Kittell | |
| 5,492,118 A | 2/1996 | Gratton et al. | |
| 5,506,482 A | 4/1996 | Teramatsu | |
| 5,507,288 A | 4/1996 | Bocker et al. | |
| 5,517,301 A | 5/1996 | Dave | |
| 5,548,674 A | 8/1996 | Rondeau | |
| 5,574,855 A | 11/1996 | Rosich et al. | |
| 5,596,987 A | 1/1997 | Chance | |
| 5,619,195 A | 4/1997 | Allen | |
| 5,632,273 A | 5/1997 | Suzuki | |
| 5,636,634 A | 6/1997 | Kordis | |
| 5,655,530 A | 8/1997 | Messerschmidt | |
| 5,661,843 A | 8/1997 | Rickenbach | |
| 5,671,317 A | 9/1997 | Weishaupt | |
| 5,687,717 A | 11/1997 | Halpern et al. | |
| 5,725,480 A | 3/1998 | Ooste | |
| 5,730,140 A | 3/1998 | Fitch | |
| 5,747,806 A | 5/1998 | Khalil et al. | |
| 5,750,994 A | 5/1998 | Schlager | |
| 5,769,076 A | 6/1998 | Maekawa | |
| 5,770,454 A | 6/1998 | Essenpreis et al. | |
| 5,823,951 A | 10/1998 | Messerschmidt | |
| 5,825,488 A | 10/1998 | Kohl et al. | |
| 5,830,132 A | 11/1998 | Robinson | |
| 5,869,075 A | 2/1999 | Krzysik | |
| 5,877,664 A | 3/1999 | Jackson, Jr. | |
| 5,879,373 A | 3/1999 | Roper et al. | |
| 5,891,021 A | 4/1999 | Dillon | |
| 5,912,656 A | 6/1999 | Tham et al. | |
| 5,935,062 A | 8/1999 | Messerschmidt et al. | |
| 5,945,676 A | 8/1999 | Khalil et al. | |
| 5,956,150 A | 9/1999 | Kanne | |
| 5,978,691 A | 11/1999 | Mills | |
| 6,014,756 A | 1/2000 | Dottling | |
| 6,040,578 A | 3/2000 | Malin et al. | |
| 6,045,511 A | 4/2000 | Ott | |
| 6,067,463 A | 5/2000 | Jeng et al. | |
| 6,088,605 A | 7/2000 | Griffith et al. | |
| 6,093,156 A | 7/2000 | Cunningham et al. | |
| 6,095,974 A | 8/2000 | Shemwell et al. | |
| 6,115,673 A | 9/2000 | Malin et al. | |
| 6,144,868 A | 11/2000 | Parker | |
| 6,147,749 A | 11/2000 | Kubo et al. | |
| 6,152,876 A | 11/2000 | Robinson | |
| 6,157,041 A | 12/2000 | Thomas et al. | |
| 6,180,416 B1 | 1/2001 | Kuenik et al. | |
| 6,230,034 B1 | 5/2001 | Messerschmidt | |
| 6,233,471 B1 | 5/2001 | Berner et al. | |
| 6,236,047 B1 | 5/2001 | Malin et al. | |
| 6,240,306 B1 | 5/2001 | Rohrscheib et al. | |
| 6,253,097 B1 | 6/2001 | Aronow et al. | |
| 6,272,364 B1 | 8/2001 | Kurnik | |
| 6,280,381 B1 | 8/2001 | Malin et al. | |
| 6,289,230 B1 | 9/2001 | Chaiken et al. | |
| 6,304,766 B1 | 10/2001 | Colvin, Jr. | |
| 6,326,160 B1 | 12/2001 | Dunn et al. | |
| 6,330,464 B1 | 12/2001 | Colvin, Jr. et al. | |
| 6,334,360 B1 | 1/2002 | Chen | |
| 6,381,489 B1 | 4/2002 | Ashibe | |
| 6,400,974 B1 | 6/2002 | Lesho | |
| 6,405,065 B1 | 6/2002 | Malin et al. | |
| 6,411,373 B1 | 6/2002 | Garside et al. | |
| 6,411,838 B1 | 6/2002 | Nordstrom et al. | |
| 6,415,167 B1 | 7/2002 | Blank et al. | |
| 6,421,549 B1 | 7/2002 | Jacques | |
| 6,441,388 B1 | 8/2002 | Thomas | |
| 6,442,408 B1 | 8/2002 | Wenzel et al. | |
| 6,449,500 B1 | 9/2002 | Asai et al. | |
| 6,456,870 B1 | 9/2002 | Rennert et al. | |
| 6,475,800 B1 | 11/2002 | Hazen et al. | |
| 6,487,429 B2 | 11/2002 | Hockersmith et al. | |
| 6,493,566 B1 | 12/2002 | Ruchti et al. | |
| 6,501,982 B1 | 12/2002 | Ruchti et al. | |
| 6,507,687 B1 | 1/2003 | Juskaitis et al. | |
| 6,512,937 B2 | 1/2003 | Blank et al. | |
| 6,512,982 B2 | 1/2003 | Yang et al. | |
| 6,528,809 B1 | 3/2003 | Thomas | |
| 6,546,269 B1 | 4/2003 | Kurnik | |
| 6,558,320 B1 | 5/2003 | Causey et al. | |
| 6,574,490 B2 | 6/2003 | Abbink et al. | |
| 6,585,370 B2 | 7/2003 | Zelman | |
| 6,631,282 B2 | 10/2003 | Rule et al. | |
| 6,641,533 B2 | 11/2003 | Causey, III et al. | |
| 6,690,958 B1 * | 2/2004 | Walker et al. ............... 600/323 |
| 6,788,965 B2 | 9/2004 | Ruchti | |
| 6,839,583 B1 | 1/2005 | Lewandowski et al. | |
| 6,920,345 B2 | 7/2005 | Al-Ali et al. | |
| 6,927,843 B2 * | 8/2005 | Dick .......................... 600/315 |
| 7,133,710 B2 | 11/2006 | Acosta et al. | |
| 7,178,063 B1 | 2/2007 | Smith | |
| 7,409,330 B2 | 8/2008 | Kumamoto | |
| 2002/0026106 A1 | 2/2002 | Khalil et al. | |
| 2002/0058864 A1 | 5/2002 | Mansfield | |
| 2002/0087949 A1 | 7/2002 | Golender et al. | |
| 2003/0040663 A1 | 2/2003 | Rule | |
| 2003/0156270 A1 | 8/2003 | Hunter | |
| 2003/0208113 A1 | 11/2003 | Mault et al. | |
| 2003/0216627 A1 | 11/2003 | Lorenz | |
| 2003/0216630 A1 | 11/2003 | Jersey-Willuhn et al. | |
| 2004/0068163 A1 | 4/2004 | Ruchti | |
| 2004/0077937 A1 | 4/2004 | Yarden | |
| 2004/0127777 A1 | 7/2004 | Ruchti | |
| 2004/0163032 A1 | 8/2004 | Guo | |
| 2004/0167473 A1 | 8/2004 | Moenning | |
| 2005/0007125 A1 | 1/2005 | Heger | |
| 2005/0034102 A1 | 2/2005 | Peck | |
| 2005/0054908 A1 | 3/2005 | Blank et al. | |
| 2005/0187439 A1 | 8/2005 | Blank et al. | |
| 2005/0267342 A1 | 12/2005 | Blank et al. | |
| 2006/0200017 A1 | 9/2006 | Monfre et al. | |
| 2006/0211931 A1 | 9/2006 | Blank et al. | |
| 2006/0217602 A1 | 9/2006 | Abul-Haj et al. | |
| 2008/0009835 A1 | 1/2008 | Kriesel et al. | |
| 2008/0033275 A1 | 2/2008 | Blank et al. | |
| 2009/0062635 A1 | 3/2009 | Brauker et al. | |

FOREIGN PATENT DOCUMENTS

| | | |
|---|---|---|
| DE | 2640987 | 3/1978 |
| EP | 1254631 | 11/2002 |
| JP | 04-215742 | 8/1992 |
| JP | 05-317295 | 12/1993 |
| JP | 08-215180 | 8/1996 |
| JP | 2001-037741 | 2/2001 |
| JP | 2001-299727 | 10/2001 |
| JP | 2002535023 | 10/2002 |
| WO | WO 96/28084 | 9/1996 |
| WO | WO 97/05819 | 2/1997 |
| WO | WO 97/28437 | 8/1997 |
| WO | WO 00/22982 | 4/2000 |
| WO | WO 00/42907 | 7/2000 |
| WO | WO 00/74562 | 12/2000 |
| WO | WO 00/76573 A3 | 12/2000 |
| WO | WO 01/31304 | 5/2001 |
| WO | WO 01/58355 | 8/2001 |

| WO | WO 0172222 A1 * | 10/2001 |
| WO | WO 01/82794 | 11/2001 |
| WO | WO 02/065090 | 8/2002 |

OTHER PUBLICATIONS

Barnes, R.J. et al., "Standard Normal Variate Transformation and De-trending of Near-Infrared Diffuse Reflectance Spectra", Applied Spectroscopy, 1989, pp. 772-777, vol. 43, No. 5.

Beebe, K.R., et al., Chemometrics: A Practical Guide, 1998, pp. 26-55, John Wiley & Sons, Inc., New York.

Blank, T.B., et al., "Transfer of Near-Infrared Multivariate Calibrations without Standards", Analytical Chemistry, 1996, pp. 2987-2995, vol. 68.

Cygnus, Inc., "GlucoWatch Automatic Glucose Biographer and AutoSensors", Cygnus Inc., Revision date: Mar. 2001, Document #1992-00.

The Diabetes Control and Complications Trial Research Group, "The Effect of Intensive Treatment of Diabetes on the Development and Progression of Long-Term Complications in Insulin-Dependent Diabetes Mellitus", N Eng J of Med, Sep. 30, 1993, pp. 977-986, vol. 329, No. 14.

Diabetes Statistics, NIDDK National Diabetes Information Clearinghouse, Nov. 1997, National Institute of Health, Bethesda, MD; NIH Publication No. 98-3926, http://www.niddk.nih.gov; Retrieved Jan. 22, 1999.

Geladi, P., et al., "Linearization and Scatter-Corrections for Near-Infrared Reflectance Spectra of Meat", Applied Spectroscopy, 1985, pp. 491-500, vol. 39, No. 3.

Gross, T.M., et al., "Performance Evaluation of the MiniMed Continuous Glucose Monitoring System During Patient Home Use", Diabetes Technology & Therapeutics, 2000, pp. 49-56, vol. 2, No. 1.

Hazen, K.H., "Glucose Determination in Biological Matrices Using Near-Infrared Spectroscopy", Doctoral Dissertation, University of Iowa, Aug. 1995, pp. 193-203 & 242-249.

Isaksson, T., et al., "Optimised Scaling (OS-2) Regression Applied to Near Infrared Diffuse Spectroscopy Data from Food Products", J. Near Infrared Spectroscopy, 1993, pp. 85-97, vol. 1.

Isaksson, T., et al., "Piece-Wise Multiplicative Scatter Correction Applied to Near-Infrared Diffuse Transmittance Data from Meat Products", Applied Spectroscopy, 1993, pp. 702-709, vol. 47, No. 6.

Martens, H., et al., "Extended Multiplicative Signal Correction and Spectral Interference Subtraction: New Preprocessing Methods of Near-Infrared Spectroscopy", Journal of Pharmaceutical & Biomedical Analysis, 1991, pp. 625-635, vol. 9, No. 8.

Massart, D.L., et al., "Data Handling in Science and Technology—vol. 2", Chemometrics: a textbook, 1988, pp. 215-253, Elsevier Science Publishing Company, Inc., New York.

Ohkudo, Y., et al., "Intensive Insulin Therapy Prevents the Progression of Diabetic Microvascular Complications in Japanese Patients with Non-Insulin-Dependent Diabetes Mellitus: A Randomized Prospective 6-Year Study", Diabetes Research and Clinical Practice, 1995, pp. 103-117, vol. 28.

Oppenheim, A.V., et al., "Digital Filter Design Techniques", Digital Signal Processing, 1975, pp. 195-271, Prentice Hall, Englewood Cliffs, New Jersey.

Otto, M., Chemometrics, Statistics and Computer Application in Analytical Chemistry, 1999, pp. 51-78, Wiley-VCH, New York.

Rebrin, K., et al., "Subcutaneous Glucose Predicts Plasma Glucose Independent of Insulin: Implications for Continuous Monitoring", American Journal of Physiology, 1999, vol. 277, pp. E561-E571, 0193-1849/99, The American Physiological Society.

Savitsky, A., et al., "Smoothing and Differentiation of Data by Simplified Least Squares Procedures", Analytical Chemistry, Jul. 1964, pp. 1627-1639, vol. 36, No. 8.

Sharaf, M.A., et al., Chemometrics, 1986, pp. 102-109, John Wiley & Sons, New York.

Sum, S.T., "Spectral Signal Correction for Multivariate Calibration", Doctoral Dissertation, University of Delaware, 1998, pp. 92-136.

Sum, S.T., et al., "Standardization of Fiber-Optic Probes for Near-Infrared Multivariate Calibrations", Applied Spectroscopy, 1998, pp. 869-877, vol. 52, No. 6.

Tamada, J.A., et al., "Noninvasive Glucose Monitoring Comprehensive Clinical Results", JAMA, Nov. 17, 1999, pp. 1839-1844, vol. 282, No. 19.

Tranjanoski, Z., et al., "Open-Flow Microperfusion of Subcutaneous Adipose Tissue for On-Line Continuous Ex Vivo Measurement of Glucose Concentration", Diabetes Care, Jul. 1997, pp. 1114-1120, vol. 20, No. 7.

Tranjanoski, Z., et al., "Portable Device for Continuous Fractionated Blood Sampling and Continuous Ex Vivo Blood Glucose Monitoring", Biosensors & Bioelectronics, 1996, vol. 11, No. 5, pp. 479-487.

U.K. Prospective Diabetes Study (UKPDS) Group, "Intensive Blood-Glucose Control with Sulphonylureas or Insulin Compared with Conventional Treatment and Risk of Complications in Patients with Type 2 Diabetes (UKPDS 33)", Lancet, Sep. 12, 1998, pp. 837-853, vol. 352.

* cited by examiner

NONINVASIVE TARGETING SYSTEM METHOD AND APPARATUS

CROSS REFERENCE TO RELATED APPLICATIONS

This Application:
claims benefit of U.S. provisional patent application No. 60/656,727 filed Feb. 25, 2005;
claims benefit of U.S. provisional patent application No. 60/658,708 filed Mar. 3, 2005; and
claims benefit of U.S. provisional patent application No. 60/658,821 filed Mar. 4, 2005; and all of which are incorporated as if fully set forth herein in their entirety by this reference thereto.

BACKGROUND OF THE INVENTION

1. Field of the Invention

The invention relates to noninvasive sampling. More particularly, the invention relates to a sample probe interface method and apparatus for use in conjunction with a noninvasive analyzer. More particularly, the invention relates to a targeting system used to control sampling position of a measuring system where control of positioning of the measuring system enhances noninvasive analyte property determination.

2. Description of Related Art

A wide range of technologies serve to analyze the chemical make-up of the body. These techniques are broadly categorized into two groups, invasive and noninvasive. Herein, a technology is referred to as invasive if the measurement process acquires a biosample from the body for analysis or if any part of the measuring apparatus penetrates through the outer layers of skin into the body. Noninvasive procedures do not penetrate into the body or acquire a biosample outside of their calibration and calibration maintenance steps.

Invasive

Some examples of invasive technologies for glucose concentration determination in the body are those that analyze the biosamples of whole blood, serum, plasma, interstitial fluid, and mixtures or selectively sampled components of the aforementioned. Typically, these samples are analyzed with electrochemical, electroenzymatic, and/or colorimetric approaches. For example, enzymatic and colorimetric approaches are used to determine the glucose concentration in interstitial fluid samples.

Noninvasive

Noninvasive analyzers deliver external energy in the form of light to a sample site, region, or volume of the human body where the photons interact with a tissue sample, thus probing chemical and physical features. Some of the incident photons are specularly reflected, diffusely reflected, scattered and/or transmitted out of the body where they are detected. Based upon knowledge of the incident photons and detected photons, the chemical and/or structural basis of the sampled site is deduced. A distinct advantage of a noninvasive analyzer is the analysis of chemical and structural constituents in the body without the generation of a biohazard in a pain-free manner with limited consumables. Additionally, noninvasive analyzers allow multiple analytes or structural features to be determined at one time. Common examples of noninvasive analyzers are magnetic resonance imaging (MRI's), X-rays, pulse oximeters, and noninvasive glucose concentration analyzers. With the exception of X-rays, these determinations are performed with relatively harmless wavelengths of radiation.

Examples herein focus on noninvasive glucose concentration estimation using near-infrared vibrational absorption spectroscopy, but the principles apply to other noninvasive measurements and/or estimation of additional blood and/or tissue analytes.

Noninvasive Glucose Concentration Estimation

There exist a number of noninvasive approaches for glucose concentration estimation in tissue or blood. These approaches vary widely but have at least two common steps. First, an apparatus is used to acquire a photometric signal from the body, typically without obtaining a glucose concentration estimation. Second, an algorithm is used to convert this signal into a glucose concentration estimation.

One type of noninvasive glucose concentration analyzer is a system performing glucose concentration estimations from spectra. Typically, a noninvasive apparatus uses some form of spectroscopy to acquire a signal, such as a spectrum, from the body. A particular range for noninvasive glucose concentration estimation in diffuse reflectance mode is in the near-infrared from approximately 1100 to 2500 nm or one or more ranges therein. These techniques are distinct from traditional invasive and alternative invasive techniques in that the interrogated sample is a portion of the human body in-situ, not a biological sample acquired from the human body.

Calibration

Optical based glucose concentration analyzers require calibration. This is true for all types of glucose concentration analyzers, such as traditional invasive, alternative invasive, noninvasive, and implantable analyzers. A fundamental feature of noninvasive glucose analyzers is that they are secondary in nature, that is, they do not measure blood glucose concentrations directly. Therefore, a primary method is required to calibrate these devices to measure blood glucose concentrations properly.

Instrumentation

There are a number of reports on noninvasive glucose technologies. Some of these relate to general instrumentation configurations required for noninvasive glucose concentration estimation while others refer to sampling technologies. Those related to the present invention are briefly reviewed here:

P. Rolfe, Investigating substances in a patient's bloodstream, U.K. patent application ser. no. 2,033,575 (Aug. 24, 1979) describes an apparatus for directing light into the body, detecting attenuated backscattered light, and using the collected signal to determine glucose concentrations in or near the bloodstream.

C. Dahne, D. Gross, Spectrophotometric method and apparatus for the non-invasive, U.S. Pat. No. 4,655,225 (Apr. 7, 1987) describe a method and apparatus for directing light into a patient's body, collecting transmitted or backscattered light, and determining glucose concentrations from selected near-infrared infrared wavelength bands. Wavelengths include 1560 to 1590, 1750 to 1780, 2085 to 2115, and 2255 to 2285 nm with at least one additional reference signal from 1000 to 2700 nm.

R. Barnes, J. Brasch, D. Purdy, W. Lougheed, Non-invasive determination of analyte concentration in body of mammals, U.S. Pat. No. 5,379,764 (Jan. 10, 1995) describe a noninvasive glucose concentration estimation analyzer that uses data pretreatment in conjunction with a multivariate analysis to estimate blood glucose concentrations.

M. Robinson, K. Ward, R. Eaton, D. Haaland, Method and apparatus for determining the similarity of a biological analyte from a model constructed from known biological fluids, U.S. Pat. No. 4,975,581 (Dec. 4, 1990) describe a method and apparatus for measuring a concentration of a biological analyte, such as glucose concentration, using infrared spectroscopy in conjunction with a multivariate model. The multivariate model is constructed from a plurality of known biological fluid samples.

J. Hall, T. Cadell, Method and device for measuring concentration levels of blood constituents non-invasively, U.S. Pat. No. 5,361,758 (Nov. 8, 1994) describe a noninvasive device and method for determining analyte concentrations within a living subject using polychromatic light, a wavelength separation device, and an array detector. The apparatus uses a receptor shaped to accept a fingertip with means for blocking extraneous light.

S. Malin, G Khalil, Method and apparatus for multi-spectral analysis of organic blood analytes in noninvasive infrared spectroscopy, U.S. Pat. No. 6,040,578 (Mar. 21, 2000) describe a method and apparatus for determination of an organic blood analyte using multi-spectral analysis in the near-infrared. A plurality of distinct nonoverlapping regions of wavelengths are incident upon a sample surface, diffusely reflected radiation is collected, and the analyte concentration is determined via chemometric techniques.

Specular Reflectance

R. Messerschmidt, D. Sting Blocker device for eliminating specular reflectance from a diffuse reflectance spectrum, U.S. Pat. No. 4,661,706 (Apr. 28, 1987) describe a reduction of specular reflectance by a mechanical device. A blade-like device "skims" the specular light before it impinges on the detector. A disadvantage of this system is that it does not efficiently collect diffusely reflected light and the alignment is problematic.

R. Messerschmidt, M. Robinson Diffuse reflectance monitoring apparatus, U.S. Pat. No. 5,636,633 (Jun. 10, 1997) describe a specular control device for diffuse reflectance spectroscopy using a group of reflecting and open sections.

R. Messerschmidt, M. Robinson Diffuse reflectance monitoring apparatus, U.S. Pat. No. 5,935,062 (Aug. 10, 1999) and R. Messerschmidt, M. Robinson Diffuse reflectance monitoring apparatus, U.S. Pat. No. 6,230,034 (May 8, 2001) describe a diffuse reflectance control device that discriminates between diffusely reflected light that is reflected from selected depths. This control device additionally acts as a blocker to prevent specularly reflected light from reaching the detector.

Malin, supra describes the use of specularly reflected light in regions of high water absorbance, such as 1450 and 1900 nm, to mark the presence of outlier spectra wherein the specularly reflected light is not sufficiently reduced.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sampling medium to minimize specular reflectance. Further, the apparatus allows for reproducible applied pressure to the sampling site and reproducible temperature at the sampling site.

Temperature

K. Hazen, *Glucose Determination in Biological Matrices Using Near-Infrared Spectroscopy*, doctoral dissertation, University of Iowa (1995) describes the adverse effect of temperature on near-infrared based glucose concentration estimations. Physiological constituents have near-infrared absorbance spectra that are sensitive, in terms of magnitude and location, to localized temperature and the sensitivity impacts noninvasive glucose concentration estimation.

Pressure

E. Chan, B. Sorg, D. Protsenko, M. O'Neil, M. Motamedi, A. Welch, *Effects of compression on soft tissue optical properties*, IEEE Journal of Selected Topics in Quantum Electronics, Vol. 2, no. 4, pp. 943-950 (1996) describe the effect of pressure on absorption and reduced scattering coefficients from 400 to 1800 nm. Most specimens show an increase in the scattering coefficient with compression.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe in a first embodiment a noninvasive glucose concentration estimation apparatus for either varying the pressure applied to a sample site or maintaining a constant pressure on a sample site in a controlled and reproducible manner by moving a sample probe along the z-axis perpendicular to the sample site surface. In an additional described embodiment, the arm sample site platform is moved along the z-axis that is perpendicular to the plane defined by the sample surface by raising or lowering the sample holder platform relative to the analyzer probe tip. The '012 patent further teaches proper contact to be the moment specularly reflected light is about zero at the water bands about 1950 and 2500 nm.

Coupling Fluid

A number of sources describe coupling fluids with important sampling parameters.

Index of refraction matching between the sampling apparatus and sampled medium is well known. Glycerol is a common index matching fluid for optics to skin.

R. Messerschmidt, Method for non-invasive blood analyte measurement with improved optical interface, U.S. Pat. No. 5,655,530 (Aug. 12, 1997), and R. Messerschmidt Method for non-invasive blood analyte measurement with improved optical interface, U.S. Pat. No. 5,823,951 (Oct. 20, 1998) describe an index-matching medium for use between a sensor probe and the skin surface. The index-matching medium is a composition containing perfluorocarbons and chlorofluorocarbons.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,306 (May 29, 2001) describe an index-matching medium to improve the interface between the sensor probe and skin surface during spectroscopic analysis. The index-matching medium is preferably a composition containing chlorofluorocarbons with optional added perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more perfluoro compounds where a quantity of the coupling fluid is placed at an interface of the optical probe and measurement site. Perfluoro compounds do not have the toxicity associated with chlorofluorocarbons.

M. Makarewicz, M. Mattu, T. Blank, G. Acosta, E. Handy, W. Hay, T. Stippick, B. Richie, Method and apparatus for minimizing spectral interference due to within and between sample variations during in-situ spectral sampling of tissue, U.S. patent application Ser. No. 09/954,856 (filed Sep. 17, 2001) describe a temperature and pressure controlled sample interface. The means of pressure control are a set of supports for the sample that control the natural position of the sample probe relative to the sample.

Positioning

E. Ashibe, Measuring condition setting jig, measuring condition setting method and biological measuring system, U.S. Pat. No. 6,381,489, Apr. 30, 2002 describes a measurement condition setting fixture secured to a measurement site, such as a living body, prior to measurement. At time of measurement, a light irradiating section and light receiving section of a measuring optical system are attached to the setting fixture to attach the measurement site to the optical system.

J. Röper, D. Böcker, System and method for the determination of tissue properties, U.S. Pat. No. 5,879,373 (Mar. 9, 1999) describe a device for reproducibly attaching a measuring device to a tissue surface.

J. Griffith, P. Cooper, T. Barker, Method and apparatus for non-invasive blood glucose sensing, U.S. Pat. No. 6,088,605 (Jul. 11, 2000) describe an analyzer with a patient forearm interface in which the forearm of the patient is moved in an incremental manner along the longitudinal axis of the patient's forearm. Spectra collected at incremental distances are averaged to take into account variations in the biological components of the skin. Between measurements rollers are used to raise the arm, move the arm relative to the apparatus and lower the arm by disengaging a solenoid causing the skin lifting mechanism to lower the arm into a new contact with the sensor head.

T. Blank, G. Acosta, M. Mattu, S. Monfre, Fiber optic probe guide placement guide, U.S. Pat. No. 6,415,167 (Jul. 2, 2002) describe a coupling fluid and the use of a guide in conjunction with a noninvasive glucose concentration analyzer in order to increase precision of the location of the sampled tissue site resulting in increased accuracy and precision in noninvasive glucose concentration estimations.

T. Blank, G. Acosta, M. Mattu, M. Makarewicz, S. Monfre, A. Lorenz, T. Ruchti, Optical sampling interface system for in-vivo measurement of tissue, world patent publication no. WO 2003/105664 (filed Jun. 11, 2003) describe an optical sampling interface system that includes an optical probe placement guide, a means for stabilizing the sampled tissue, and an optical coupler for repeatably sampling a tissue measurement site in-vivo.

To date, accurate and precise noninvasive analyte property determination have not been generated in a reproducible fashion, largely due to sampling variation and changes in the tissue state. A solution to the problem is to use a targeting system for precisely locating a sample volume and an adaptive measuring system to relieve induced strain on the sample site between and during sampling. The adaptive measuring system reduces stress and strain and/or has improved sampling precision and accuracy leading to enhanced noninvasive analyte property estimation.

The method and apparatus result in:
increased precision and accuracy of noninvasive sampling;
a means of assuring that the similar tissue sample volumes are repeatably sampled; and
minimizing sampling errors due to mechanical tissue distortion and probe placement.

SUMMARY OF THE INVENTION

The invention provides a targeting system used to direct a measuring system to a targeted sample site or volume. The targeting system increases analyte estimation performance by increasing precision and accuracy of sampling and/or by targeting an analyte rich tissue volume.

DETAILED DESCRIPTION OF THE INVENTION

Sampling is controlled to enhance analyte concentration estimation derived from noninvasive sampling. A targeting system is used to direct a measuring system to a targeted tissue sample site or tissue volume. The targeting system increases analyte estimation performance by increasing precision and/or accuracy of sampling and/or by targeting an analyte rich tissue volume.

Analyzer

An analyzer includes two major elements, a targeting system and a measuring system. The measuring system is integral to the analyzer. The targeting system is optionally internal to the analyzer, semi-coupled to the analyzer, or is used separately from the analyzer in terms of time of use or in the space that is occupied.

Coordinate System

Herein, an x, y, and z-axes coordinate system relative to a given body part is defined. An x,y,z coordinate system is used to define the sample site, movement of objects about the sample site, changes in the sample site, and physical interactions with the sample site. The x-axis is defined along the length of a body part and the y-axis is defined across the body part. As an illustrative example using a sample site on the forearm, the x-axis runs between the elbow and the wrist and the y-axis runs across the axis of the forearm. Similarly, for a sample site on a digit of the hand, the x-axis runs between the base and tip of the digit and the y-axis runs across the digit. Together, the x,y plane tangentially touches the skin surface, such as at a sample site. The z-axis is defined as orthogonal to the plane defined by the x- and y-axes. For example, a sample site on the forearm is defined by an x,y plane tangential to the sample site. An object, such as a sample probe, moving along an axis perpendicular to the x,y plane is moving along the z-axis. Rotation of an object about one or a combination of axes is further used to define the orientation of an object, such as a sample probe, relative to the sample site. Tilt refers to an off z-axis alignment of the longitudinal orientation of the sample probe where the longitudinal axis extends from the sample probe tip interfacing with a sample site to the opposite end of the sample probe.

Measuring System/Targeting System

Figure 1:
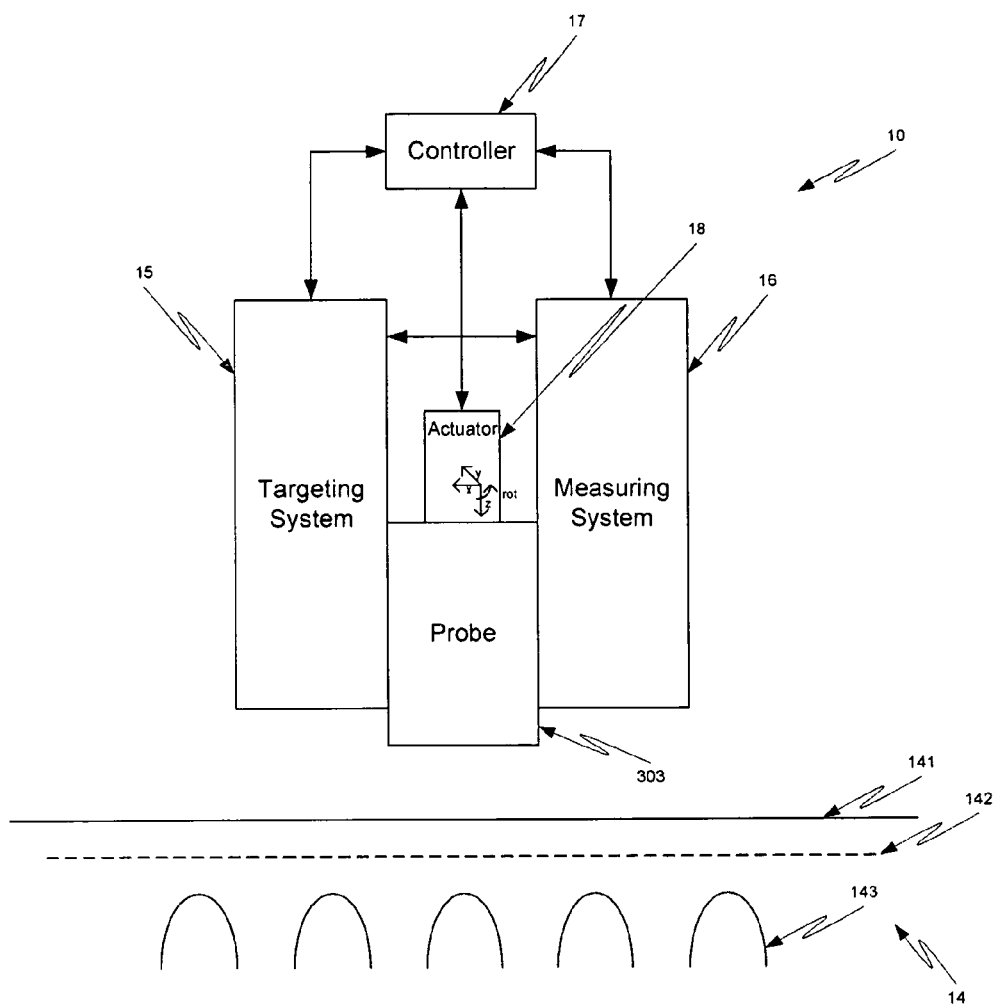
FIG. 1 provides a block diagram of an analyzer with a targeting system and a measuring system according to the invention.

Referring now to FIG. 1, a block diagram of an analyzer 10 is presented. The analyzer has two primary systems, a targeting system 15 and a measuring system 16. The targeting system targets a tissue area or volume of the sample 14. For example, the targeting system targets a surface feature 141, one or more volumes or layers 142, and/or an underlying feature 143, such as a capillary, blood vessel, and/or a distance between a portion of the measuring system, such as a sample probe tip and the sample site. The measuring system contains a sample probe 303, which is optionally separate from or integrated into the targeting system. The sample probe of the measuring system is preferably directed to the targeted region or to a location relative to the targeted region either while the targeting system is active or subsequent to targeting. Less preferably, use of the measuring system is followed by use of the targeting system and a targeting image is used to post process the measuring system data. A controller 17 is used to direct the movement of the sample probe 303 in at least one of the x-, y-, and z-axes via one or more actuators 18. Optionally the controller directs a part of the analyzer that changes the observed tissue sample in terms of surface area or volume. The controller communicates with the targeting system, measuring system, and/or controller.

There exist a large number of targeting and measuring system configurations. Several exemplar embodiments are provided, infra. Some features of the configurations are outlined here. The targeting system and measuring system optionally use a single source that is shared or have separate sources. The targeting is optionally used to first target a region and the measuring system is used to subsequently sample at or near the targeted region. Alternatively, the targeting and measuring system are used over the same period of time so that targeting is active during sampling by the measuring system. The targeting system and measuring system optionally share optics and/or probe the same tissue area and/or volume. Alternatively, the targeting and measuring system use separate optics and/or probe different or overlapping tissue volumes. In various configurations, neither, one, or both of the targeting system and measuring system are brought into contact with the skin tissue 14 at or about the sample site. Each of these parameters are further considered, infra. Finally, permutations and combinations of the strategies and components of the embodiments presented herein are possible.

The targeting system targets a target. Targets include any of:

- a natural tissue component;
- a chemical feature;
- a physical feature;
- an abstract feature;
- a marking feature added to the skin;
- a skin surface feature;
- a measurement of tissue strain;
- tissue morphology;
- a target below the skin surface;
- a manmade target;
- a fluorescent marker;
- a subcutaneous feature;
- a dermis thickness within a specification;
- capillary beds;
- a capillary;
- a blood vessel; and
- arterial anastomoses.

Examples of marking features added to the skin include a tattoo, one or more dyes, one or more reflectors, a crosshair marking, and positional markers, such as one or more dots or lines. Examples of a skin surface feature include a wart, hair follicle, hair, freckle, wrinkle, and gland. Tissue morphology includes surface shape of the skin, such as curvature and flatness. Examples of specifications for a dermis thickness include a minimal thickness and a maximum depth. For example, the target is a volume of skin wherein the analyte, such as glucose, concentration is higher. In this example, the measuring system is directed to image photons at a depth of the enhanced analyte concentration.

Targeting System

A targeting system targets a target. A targeting system typically includes a controller, an actuator, and a sample probe that are each described infra. Examples of targeting systems include a planarity detection system, optical coherence tomography (OCT), a proximity detector and/or targeting system, an imaging system, a two-detector system, and a single detector system. Examples of targeting system technology include: capacitance, impedance, acoustic signature, ultrasound, use of a pulsed laser to detect and determine distance, and the use of an electromagnetic field, such as radar and high frequency radio-frequency waves. Sources of the targeting system include a laser scanner, ultrasound, and light, such as ultraviolet, visible, near-infrared, mid-infrared, and far-infrared light. Detectors of the targeting system are optionally a single element, a two detector system, an imaging system, or a detector array, such as a charge coupled detector (CCD) or charge injection device or detector (CID). One use of a targeting system is to control movement of a sample probe to a sample site or location. A second example of use of a targeting system is to make its own measurement. A third use is as a primary or secondary outlier detection determination. In its broadest sense, one or more targeting systems are used in conjunction with or independently from a measurement system.

Different targeting techniques have different benefits. As a first example, mid-infrared light samples tissue surface features to the exclusion of features at a depth due to the large absorbance of water in the mid-infrared. A second example uses the therapeutic window in the near-infrared to image a tissue feature at a depth due to the light penetration ability from 700 to 1100 nm. Additional examples are targeting with light from about 1100 to 1450, about 1450 to 1900, and/or about 1900 to 2500 nm, which have progressively shallower penetration depths of about 10, 5, and 2 mm in tissue, respectively. A further example is use of visible light for targeting or imaging greater depths, such as tens of millimeters. Still an additional example is the use of a Raman targeting system, such as in WIPO international publication number WO 2005/009236 (Feb. 3, 2005), which is incorporated herein in its entirety by this reference thereto. A Raman system is capable of targeting capillaries. Multiple permutations and combinations of optical system components are available for use in a targeting system.

Capacitive Based Targeting System

In one embodiment of the invention, the targeting system uses capacitance sensors or touch sensors for determining any of:

- tilt of a sample probe relative to a sample site;
- distance of a sample probe tip to a sample site;
- x,y-position of a sample probe tip relative to a sample site;
- relative distance of a sample probe tip to a sample site; and
- contact of a sample probe tip with a sample site.

For a capacitance based targeting system, capacitance, C, is calculated according to equation 1

$$C \propto \frac{A}{d} \qquad (1)$$

where capacitance, C, is proportional to the area, A, of the capacitor divided by the distance, d, between the capacitor plates. The capacitor has two plates. The first capacitor plate is integrated or connected to the measuring system, such as at the sample module and preferably at the sample module sample probe tip. The second capacitor is the deformable material, such as a skin sample, body part, or a tissue sample site. The assumption is that the person is a capacitor. A typical adult has a capacitance of about 120 pF. The time constant of a capacitor/resistor is calculated according to equation 2

$$T = RC \qquad (2)$$

where the time constant, T, is equal to the resistance, R, times the capacitance, C. Hence, the distance between the capacitor plates is calculated through the combination of equations 1 and 2 through the measurement of the circuit time constant. For example, the time constant is the time required to trip a set voltage level, such as about 2.2 volts, given a power supply of known power, such as about 3.3 volts. The time constant is used to calculate the capacitance using equation 2. The capacitance is then used to calculate the distance or relative distance through equation 1. For example, as a distance between a sample site, such as a forearm or digit of a hand, and the capacitor plate decreases, the time constant increases and the capacitance increases. The measure of distance is used in positioning the probe at or in proximate contact with the sample site without disturbing the sample site.

In use, the distance or relative distance between the sample probe tip and the sample site is determined, preferably before the tip of the sample probe displaces localized sample site skin/tissue, which can lead to degradation of the sample integrity in terms of collected signal-to-noise ratios and/or sampling precision. Examples are used to illustrate the use of the capacitance sensor in the context of a noninvasive analyte property determination.

EXAMPLE I

In one example, the distance or relative distance between the sample probe tip and the sample site is determined using a single capacitor. The sample probe is brought into close proximity with the sample site using the time constant/distance measurement as a metric. In this manner, the sample probe is brought into close proximity to the sample site without displacing the sample site. Due to the inverse relationship between capacitance and distance, the sensitivity to distance between the sample site and the sample probe increases as the distance between the sample probe and the sample site decreases. Using capacitance sensors, the distance between the sample site and the tip of the sample probe is readily directed to a distance of less than about one millimeter. Capacitance sensors as used herein are also readily used to place the sample probe tip with a distance of less than about 0.1 millimeter to the sample site. In this example, multiple capacitors are optionally used to yield more than one distance reading between the sample probe tip and the sample site. Multiple capacitive sensors are optionally used to control tilt along x- and/or y-axes.

EXAMPLE II

In a second example, two or more capacitance sensors are optionally used for leveling the tip of the sample probe relative to the morphology of the sample site. The distance between the sample site and the probe tip is measured using two or more capacitor pairs. For example, if one capacitor reads a larger distance to the sample site than the second capacitor, then the probe tip is moved to level the probe by moving the larger distance side toward the sample, the smaller distance side away from the sample, or both. The sample probe tip tilt or angle is either moved manually or by mechanical means.

Controller

A controller controls the movement of one or more sample probes via one or more actuators. The controller optionally uses an intelligent system for locating the sample site and/or for determining surface morphology. For example, the controller hunts in the x- and y-axes for a spectral signature. In a second example, the controller moves a sample probe via the actuator toward or away from the sample along the z-axis. The controller optionally uses feedback from the targeting system, from the measurement system, or from an outside sensor in a closed-loop mechanism for deciding on targeting probe movement and for sample probe movement. In a third example, the controller optimizes a multivariate response, such as response due to chemical features or physical features. Examples of chemical features include blood/tissue constituents, such as water, protein, collagen, elastin, and fat. Examples of physical features include temperature, pressure, and tissue strain. Combinations of features are used to determine features, such as specular reflectance. For example, specular reflectance is a physical feature optionally measured with a chemical signature, such as water absorbance bands centered at about 1450, 1900, or 2600 nm. Controlled elements include any of the x-, y-, z-axis position of sampling along with rotation or tilt of the sample probe. Also optionally controlled are periods of light launch, intensity of light launch, depth of focus, and surface temperature. In a fourth example, the controller controls elements resulting in path-length and/or depth of penetration variation. For example, the controller controls an iris, rotating wheel, backreflector, or incident optic, which are each described infra.

Tissue Strain

The controller optionally moves the targeting probe and/or sample probe so as to make minimal and/or controlled contact with the sample. Strain is the elongation of material under load. Stress is a force that produces strain on a physical body. Strain is the deformation of a physical body under the action of applied force. In order for an elongated material to have strain there must be resistance to stretching. For example, an elongated spring has strain characterized by percent elongation, such as percent increase in length.

Skin contains constituents, such as collagen, that have spring-like properties. That is, elongation causes an increase in potential energy of the skin. Strain induced stress changes optical properties of skin, such as absorbance and scattering. Therefore, it is undesirable to make optical spectroscopy measurements on skin with various stress states. Stressed skin also causes fluid movements that are not reversible on a short timescale. The most precise optical measurements would therefore be conducted on skin in the natural strain state, such as minimally stretched skin. Skin is stretched or elongated by applying loads to skin along any of the x-, y-, and z-axes, described infra. Controlled contact reduces stress and strain on the sample. Reducing stress and strain on the sample results in more precise sampling and more accurate and precise glucose concentration estimations.

An example of using light to measure a physical property, such as contact, stress, and/or strain, in tissue is provided. Incident photons are directed at a sample and a portion of the photons returning from the sample are collected and detected. The detected photons are detected at various times, such as when no stress is applied to the tissue and when stress is applied to the tissue. For example, measurements are made when a sample probe is not yet in contact with the tissue and at various times when the sample probe is in contact with the tissue, such as immediately upon contact and with varying displacement of the sample probe into the tissue. The displacement into the tissue is optionally at a controlled or variable rate. The collected light is used to determine properties. One exemplary property is establishing contact of the sample probe with the tissue. A second exemplary property is strain. The inventors determined that different frequencies of light are indicative of different forms of stress/strain. For example, in regions of high water absorbance, such as about 1450 nm, the absorbance is indicative of water movement. Additional regions, such as those about 1290 nm, are indicative of a dermal stretch. The time constant of the response for water movement versus dermal stretch is not the same. The more fluid water movement occurs approximately twenty percent faster than the dermal stretch. The two time constants allow interpretation of the tissue state from the resultant signal. For example, the interior or subsurface hydration state is inferred from the signal. For example, a ratio of responses at high absorbance regions and low absorbance regions, such as about 1450 and 1290 nm, is made at one or more times during a measurement period. Changes in the ratio are indicative of hydration. Optionally, data collection routines are varied depending upon the determined state of the tissue. For example, the probing tissue displacement is varied with change in hydration. The strain measurement is optionally made with either the targeting system or measurement system. The tissue state probe describe herein is optionally used in conjunction with a dynamic probe, described infra.

Actuator

An actuator moves the sample probe relative to the tissue sample. One or more actuators are used to move the sample probe along one or more of the x-, y-, and z-axes. In addition, the tilt of the sample probe relative to the xy-plane tangential to the tissue sample is optionally controlled.

The targeting system operates in conjunction with the measurement system, described, infra.

Measurement System

Figure 2:
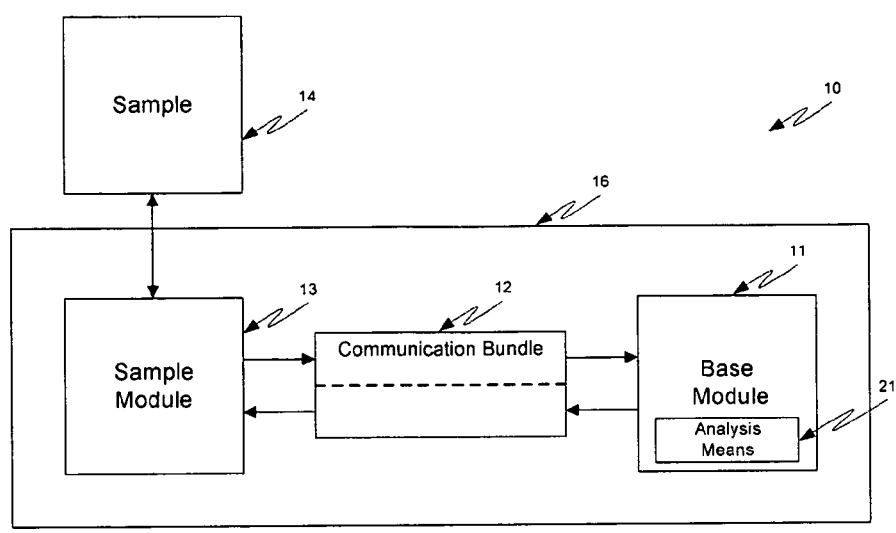
FIG. 2 provides a block diagram of a measuring system according to the invention.

Herein, the combined base module 11, communication bundle 12, sample module 13, and processing center are referred to as a measuring system 16. The combined measuring system 16 and targeting system 15 are referred to as an analyzer 10. Referring now to FIG. 2, a block diagram of an exemplar measuring system 16 of the analyzer 10 is presented that includes a base module 11 and sample module 13 connected via communication means 12, such as integrated optics or a communication bundle. In addition, analysis means 21 are incorporated into the analyzer. In an alternative embodiment, the communication bundle is replaced with wireless communication technology between the sample module and base module or the communication bundle is integrated into the analyzer.

In one example, all of the components of the measuring system 16 of the noninvasive glucose analyzer 10 are included in a single unit, such as a handheld unit or a unit. In a second example, the measuring system 16 of the analyzer 10 is physically separated into elements, such as a base module in a first housing 11, a communication bundle 12, and a sample module in a second housing 13. Advantages of separate units include heat, size, and weight management. For example, a separated base module allows for support of the bulk of the analyzer on a stable surface, such as a tabletop or floor. This allows a smaller sample module to interface with a sample, such as human skin tissue. Separation allows a more flexible and/or lighter sample module for use in sampling by an individual. Additionally, separate housing requirements are achievable for the base module and sample module in terms of power, weight, and thermal management. In addition, a split analyzer results in less of a physical impact, in terms of mass and/or tissue displacement, on the sample site by the sample module. The sample module, base module, communication bundle, display module, processing center, and tracking system are further described, infra.

Base Module

In the preferred embodiment, the base module or semi-remote system includes a wavelength selection device, such as a grating, and a detector that is preferably a detector array. The remote base module is preferably coupled to the sample via a wired or wireless communication bundle that carries at least the optical signal and optionally power. Preferably, the communication bundle transmits control and monitoring signals between the sample module and the base module. The base module preferably contains at least one of an embedded computer, a display, and an interface to an external computer system.

Sample Module

The sample/sampling module interfaces to a tissue sample site. The sample module is used to deliver photons to the sample site and to collect photons from the sample site. Optionally, any element of the analyzer is contained within the sample module. Preferably, a source, guiding optics, proximity sensor, tilt sensor, and collection optic are contained within the sample module.

In one embodiment of the invention, the base module couples directly to the sample module without a communication bundle. The combined base module and sample module are integrated into a handheld analyzer, such as a handheld near-infrared based glucose analyzer that couples to the sampling site through an optional guide.

In one preferred embodiment, the base module resides on a table, the sample module interfaces through a semi-permanently attached guide to the dorsal aspect of the forearm, and a communication bundle carries power and optical signal between the two modules. Alternatively, the base module is worn on the person, for example on a belt or as a watch is worn. The sample module alternatively couples to any of a hand, finger, palmar region, base of thumb, forearm, volar aspect of the forearm, dorsal aspect of the forearm, upper arm, head, earlobe, eye, tongue, chest, torso, abdominal region, thigh, calf, foot, plantar region, and toe. When the base module is on the table, power is preferably from a standard wall outlet for power. When worn on the person, the module is preferably battery powered. When the base module is worn on the person, an optional docking station is provided for power and data analysis.

Any of the embodiments described herein are operable in a home environment, public facility, or in a medical environment, such as an emergency room, critical care facility, intensive care unit, hospital room, or medical professional patient treatment area. For example, the split analyzer is operable in a critical care facility where the sample module is positioned in proximate contact with a subject or patient during use and where the base module is positioned on a support surface, such as a rack, medical instrumentation rack, table, or wall mount.

Optical components, such as a source, backreflector, guiding optics, lenses, filters, mirrors, a wavelength separation device, and at least one detector are optionally positioned in the base module and/or sample module.

The benefits described, supra, for controlling pressure, stress, and/or strain on the sample by controlling the movement of the targeting system sample probe relative to the tissue also apply to controlling the movement of the measurement system sample probe.

EXAMPLE III

Figure 3:
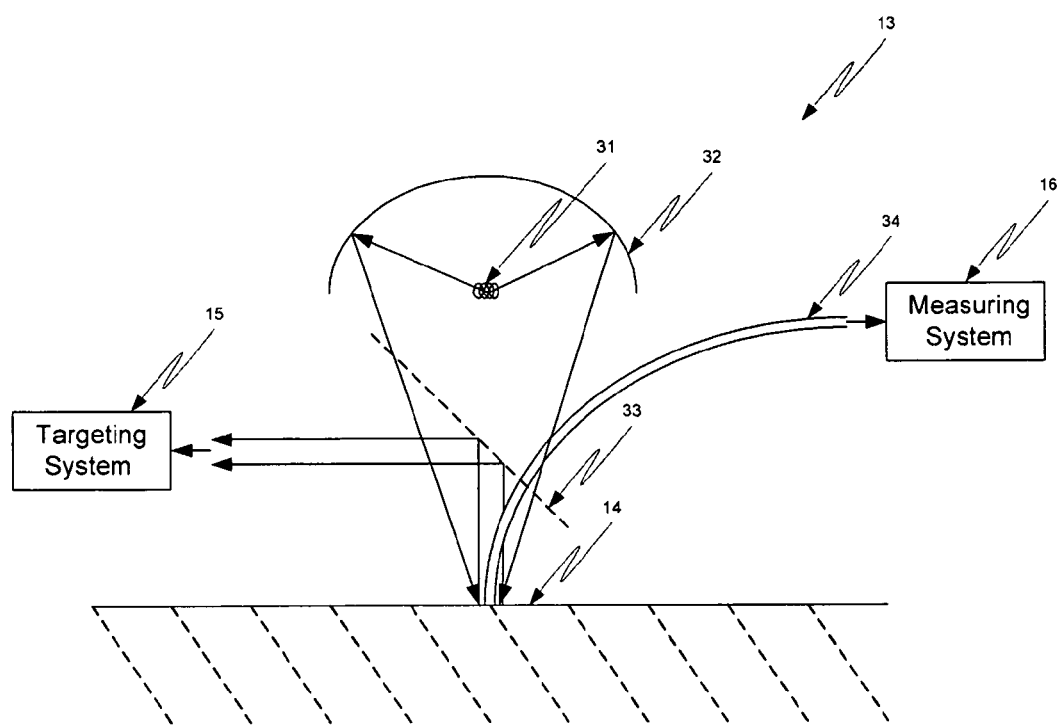
FIG. 3 is an example of an analyzer having a targeting system and a measuring system according to the invention.

In one example of the invention, a single source is used for the targeting system and the measuring system. Referring now to FIG. 3, a sample module 13 portion of an analyzer 10 is presented. Within the sample module, photons from source 31 are directed to a sample 14 either directly or via one or more optics, such as a backreflector 32 or a lens. In one case, the incident photons pass through a dichroic filter 33. A portion of the incident photons either reflect off of the surface or are diffusely reflected from a volume of the tissue sample 14. A portion of the specular and/or diffusely reflected photons are directed to a targeting system 15. In this example, the collection optics uses a dichroic filter 33 that reflects a portion of the specular or diffusely reflected to the targeting or imaging system 15. In this example, a collection optic 34, such as a fiber optic, is used to collect diffusely reflected photons. The end of the fiber optic is preferably in close proximity to the surface of the tissue sample 14. The housing or casing of the fiber optic is used to block specularly reflected light. The collected light is directed to the remainder of the measuring system 16. Optionally, coupling fluid is used at the sample module 13 skin tissue 14 interface. This example is illustrative of a system that uses a single source for the targeting system and measuring system. In addition, this example is illustrative of a system where the targeting system is used to target a sample prior to measurement or at the same time of operation of the measurement system. Still further, this example is illustrative of a targeting system that images substantially the same volume that the measuring system observes.

EXAMPLE IV

Figure 4:
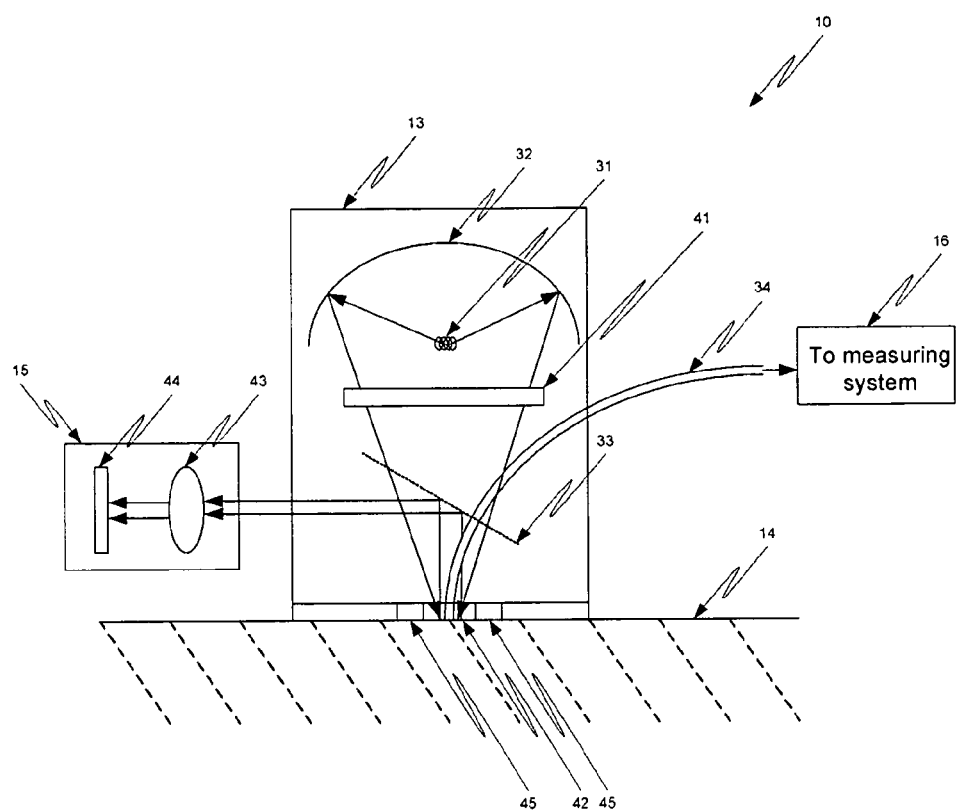
FIG. 4 is a second example of an analyzer having a targeting system and a measuring system according to the invention.

Referring now to FIG. 4, another example of the invention is provided. A sample module 13 portion of an analyzer 10 is presented. A source 31 emits light. At least part of the emitted light is incident upon a sample tissue site 14. In this example, a backreflector 32 focuses a portion of the emitted light 31 through an optional first optic 41, through an optional second optic 42, and optionally through a fluid coupler. The incident photons are optionally controlled by an aperture defined by an outer radial distance of a incident light blocker. A portion of the incident photons penetrate into the sample 14 where they are transmitted, scattered, diffusely reflected, and/or absorbed. A portion of the photons in the sample exit the sample site 14 and are directed to the targeting system 15 or measuring system 16. In the case of the targeting system 15, light is optionally directed via optics or mirrors 43 to a detector array 44. In the case of the measuring system 16, light is collected with one or more collection optics 34, such as a fiber optic. An optional guide element 45 is used to control the positioning of the incident photons.

In multiple embodiments of the invention, a first optic and a second optic are used in the optical path between the source element 31 and the tissue sample 14.

First Optic

An optional first optic 41 is placed in the optical path after the source element 31 and preferably before the tissue sample 14. In its broadest sense, the first optic includes at least one of the following parameters: optically passes desirable wavelengths of light, optically blocks at least one region of undesirable wavelengths of light, limits radiative heat transmitted to the tissue sample, and is not in contact with the tissue sample.

The first optic passes desirable wavelengths of light, such as about 1200 to 1850 nm, or sub-regions therein, such as about 1300 to 1700 nm. Within the transmissive region, high transmittance, such as greater than ninety percent, is desirable, but any transmittance is acceptable as long as sufficient net analyte signal is achieved. The first optic is, optionally, anti-reflective coated or is index of refraction matched to adjoining surfaces in the optical path. In some embodiments, such as in Example IV, the first optic also passes light used for imaging, such as a region in the visible or in the near-infrared from about 700 to 1100 nm.

The first optic preferably blocks or strongly diminishes light throughput in at least one undesirable spectral region emitted by the source or entering through ambient conditions. For example, the first optic is used to remove unwanted ultraviolet (UV), visible (VIS), and/or near-infrared light from about 700 to 1000 nm. Optionally, light of higher energy than the spectral region collected and analyzed is removed in order to remove unwanted heat resulting from photon flux onto the sample and to reduce heating of optics later in the optical path. Photons removed by the filter that result in the heating of the filter do not result in direct heating of the sample site via radiative heating or photonic heating. Rather, the much slower and less efficient conduction or convection processes convey this heat. This reduces the risk of overheating the skin at or about the sample site.

Second Optic

A second optic 42 is optionally placed in the optical path after the source element 31 and before the tissue sample 14. In its broadest senses, the second optic passes desirable wavelengths of light and/or optically blocks at least one region of undesirable wavelengths of light. The, optional, second optic is in close proximity to the tissue sample. This allows control of radiative and/or conductive heat transmitted to the tissue sample and or control of specular reflectance as described, infra.

The second optic 42 is, optionally, used to control thermal transfer to the tissue sample. In one embodiment of the invention, the second optic is of low thermal conductivity. The low thermal conductivity minimizes conductive heating of the sample by the raised temperature of the sample module 13 due to heating by the source. Examples of low thermal conductivity materials that are transmissive in the spectral region of interest include, silica, Pyrex™, sapphire, and some glasses and plastics. Optionally, the second optic has higher thermal conductivity and is used to more rapidly adjust the tissue sample 14 temperature to that of the tissue sample contacting area of the sample module 13. An example of a higher thermally conductive material is silicon.

The second optic optionally surrounds a detector or a detection optic 34, such as a fiber. An optional spacer is provided between the fiber core and the incident photons. The fiber coating and/or spacer provide specular reflectance blocking and/or depth of penetration and pathlength control as described, infra. The maximum penetration of the photons into the tissue sample preferably exceeds the radial dimension of the spacer. In this case, the second optic aids in mechanically placing or stabilizing the tip of the sample probe, preferably containing a collection fiber optic, in close proximity to the sample site.

EXAMPLE V

In a fifth example of the invention, the measuring system is used as a targeting system. The measuring system, in this example, has targeting system capabilities. The measuring system is used to both target the sample and to subsequently or concurrently measure the sample. A separate targeting system is not needed in this example.

EXAMPLE VI

Figure 5:
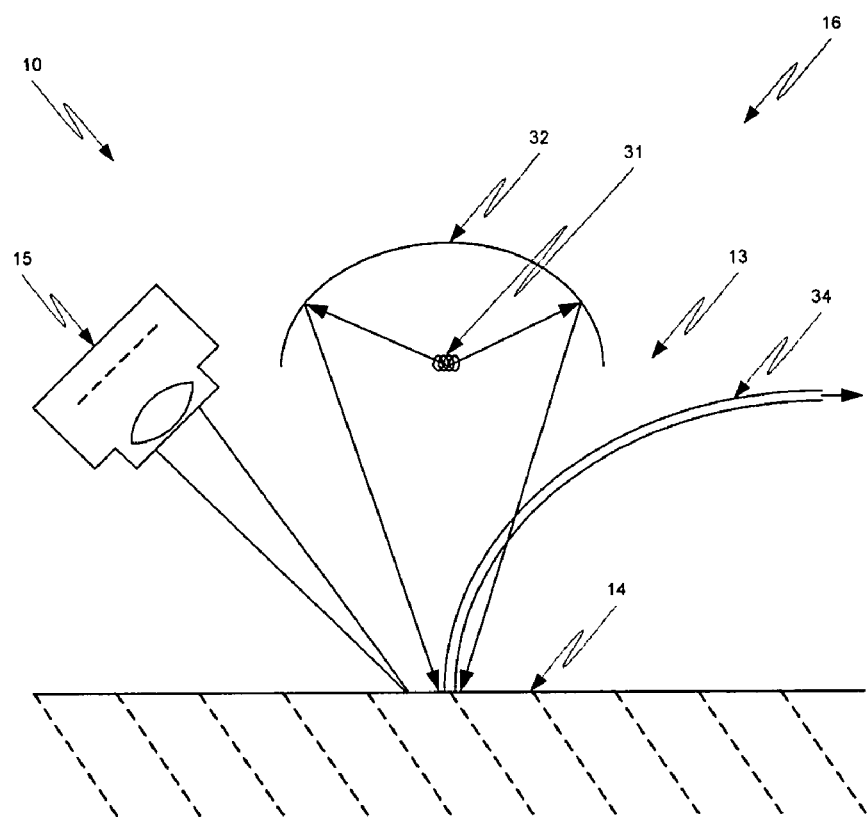
FIG. 5 is a third example of an analyzer having a targeting system and a measuring system according to the invention.

Referring now to FIG. 5, an example of a separate targeting system and sampling system is presented. The targeting system 15, such as a camera system or endoscope, targets a first tissue site or tissue volume. The measuring system 16 targets a second site or volume. The two sample sites optionally overlap, partially overlap, or are separated. Preferably, the first site and second site overlap so that the targeted site is the site sampled. Alternatively, the first site is separated from the second site. The controller is used to adjust a sample probe of the measuring system relative to the targeted volume or area. This allows the targeting system to find and target one feature and the measuring system to measure a separate feature.

In this example, the targeting system and measuring system have separate sources and optical trains. Additionally, in this example the targeting system is used before and/or concurrently in time with the measuring system.

EXAMPLE VII

Figure 6:
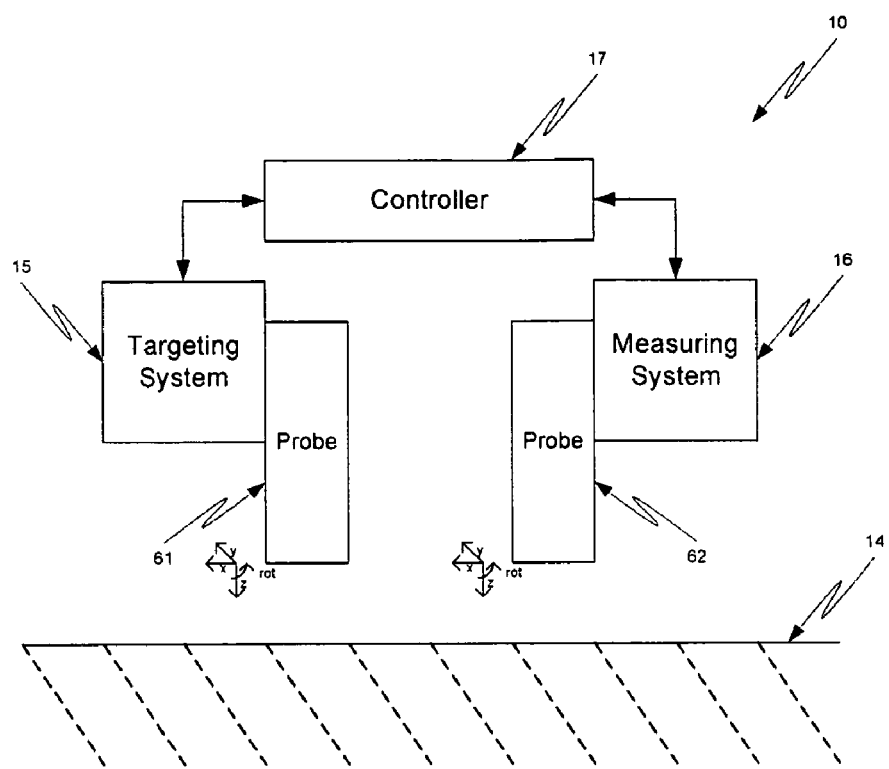
FIG. 6 provides a block diagram of a two probe analyzer according to the invention.

Referring now to FIG. 6, an example of an analyzer 10 with two separate sample probes is presented. A first sample probe 61 is part of a targeting system 15. A second sample probe 62 is part of a measuring system 16. The sample probes 61, 62 each are independently controlled via a controller 17. The sample probes move along any of the x-, y-, and z-axes and each have optional rotation and/or tilt control. The sample probes 61, 62 are used at the same or different times. The sample probes sample different tissue sample 14 locations or the same tissue sample location at different times. The two sample probes 61, 62 move in synchronization or are moved independently of each other.

Analyzer

One embodiment of the method and/or apparatus of the invention includes a targeting system used to direct sampling of a measurement system. Optional components and/or controls of the apparatus include any of:
  an adaptive sample probe head;
  a dynamic sampling probe;
  a specular reflectance blocker;
  occlusion and/or tissue hydration control;
  a coupling fluid;
  an automated coupling fluid delivery system;
  a guide;
  a mount;
  a system for reducing stress/strain on the tissue;
  a system for controlling skin tissue state;
  a split system;
  a system for controlling pathlength;
  a system for controlling depth of penetration;
  a system for reducing and/or controlling thermal changes of the skin tissue;
  means for minimizing sampling error;
  an intelligent system for data processing;
  a basis set; and/or
  a data processing algorithm.

The split system is described, supra. Optional components, processes, algorithms, or controls are briefly described, infra.

Adaptive Probe

The targeting system and/or measuring system are optionally controlled in at least one of x-, y-, and z-axes and optionally in rotation or tilt. This allows the probing system to adapt to the skin tissue surface. In this case, the sample probe is an adaptive probe with the benefit of reducing stress/strain upon sampling, as described supra.

An adaptive sample probe of the targeting and/or measuring system positions the corresponding sample probe tip at varying positions relative to a tissue sample. As the state of the skin changes, the adaptive probe adjusts the position of the sample probe tip or imaging interface relative to the tissue sample site. A first characteristic of the adaptive mount is achievement of highly repeatable sampling by limiting stress and strain on and about the median targeted tissue measurement site. In this manner, the skin undergoes minimal stress as the skin is not deformed to force the exact same position of the tissue to be sampled with each measurement. This leads to more reproducible sampling and hence better accuracy and precision of determined analyte properties.

An additional benefit of an adaptive probe is that it optionally provides a means for locally registering the location of the targeted and or measured tissue volume with respect to the optical probe and/or tip of a sample module, such that a narrow range of tissue volumes are sampled by the optical system(s). Local registration refers to controlling the position of the optical probe relative to a target and/or measurement location of the tissue. The adaptive probe allows flexibility in terms of the exact position of the tissue that is sampled. Means for registering the sample probe to the tissue are preferably optical, but are optionally mechanical and/or electromechanical.

Dynamic Sampling Probe

The sample probe is optionally dynamic. For example, the targeting system sample probe 61, the measuring system sample probe 62, and/or a shared sample probe 303 are optionally dynamic. A dynamic probe is moved in a controlled fashion relative to a tissue sample in order to control spectral variations resulting from the sample probe displacement of the tissue sample during a sampling process.

A noninvasive analyzer 10 controls movement of a dynamic sample probe along any of the x-, y-, and z-axes and optionally controls tilt and/or rotation of the sample probe relative to a sampled tissue 14. The ability to move the sample probe relative to the tissue sample as a function of time allows a dynamic tissue measurement. A dynamic tissue measurement is designed to collect time serial spectral data that contains the dynamic tissue response of the tissue sample as the sample probe is brought into contact with the tissue sample. In this measurement process spectral raster scans are collected continuously or semi-continuously as the sample probe is moved into contact with the tissue sample and/or as the sample probe displaces the tissue sample. For example, the sample probe is lowered slowly onto the targeted measurement site with or without an optical probe placement guide while the instrument acquires signal. In one case, a sample probe is controlled at least along the z-axis perpendicular to the x, y plane tangential to the surface of the sampled site thereby controlling displacement of the sample probe relative to a sample. The z-axis control of the displaced sample probe element of the sample module provides for collection of noninvasive spectra with a given displacement of a tissue sample and for collection of noninvasive spectra with varying applied displacement positions of the sample probe relative to the nominal plane of the sample tissue surface.

Specular Reflectance

The interface between the optical probe and the skin surface at the tissue measurement site is potentially a significant source of sampling error due to:
   skin state change;
   skin deformation with time;
   skin stress/strain;
   temperature mismatch;
   lost dynamic range of detection system;
   air gaps; and
   refractive index mismatch.

These issues are distinct, but have some interrelationships. Incident light normal to the surface penetrates into the skin sample based upon the difference in refractive index, Snell's Law. For the refractive index of skin, approximately 1.38, and the refractive index of air, approximately 1.0, approximately four percent of the normally incident light is reflected and ninety-six percent of the light penetrates into the skin if the surface is smooth. In practice, the rough tissue surface results in an increased percentage of specularly reflected light. In addition, the percentage of light penetrating into skin varies as the index of refraction of the interfacing material to skin changes. Further, the coupling changes with the use of an intermediate material, such as water or a coupling fluid.

The amount of light that is specularly reflected is determined to degrade noninvasive estimations of low signal to noise analytes. A targeting or measuring sample probe that does not contact the surface of the skin or is not coupled to the skin via a coupling fluid, results in specular reflectance off of the diffusely reflecting skin surface that is partially caught in collection optics. This specular reflectance is difficult to remove once captured by the collection optic system and subsequently observed with the detector system. The specular signal is often much larger in magnitude across the desired spectral region compared with the analyte signal. For example, four-percent specular light is orders of magnitude larger than a noninvasive glucose signal from the glucose molecule that is present in about the 30 to 600 mg/dL range. It is therefore beneficial to have an optical system that removes the specular component. One method for removing specular light is to have part of the sample probe contact the skin surface. For example, having an optically opaque part contact the skin between the incident and collection photons forces the collected photons to have gone through at least a portion of the skin. Examples of specular blockers include a thin or thick blade blocker or a fiber optic cladding or buffer. One or both of the targeting system and measurement system optionally has a specular blocker.

Measurement Site Occlusion/Hydration

An optional aspect of the optical sampling system of one or both of the targeting and measurement system is the maintenance of an optimal level of hydration of the surface tissue at the measurement site for enhancement of the optical signal, sample reproducibility, and suppression of surface reflectance. Skin hydration means are optionally used with the targeting and/or measuring system. Skin surface irregularities result in an increase in surface reflection of the incident light. Surface irregularities of skin mean that the incident light is not normal to the surface. This results in more reflected light, and less penetrating light. In addition, air gaps in the outer layers of skin result in more reflected light that does not penetrate to the analyte containing region. A fraction of the light penetrating into an outermost layer of skin hits one or more air pockets and is reflected off of each surface of the air pocket. Many air pockets or poor hydration lead to a significant reduction in the percentage of incident photons that penetrate through the outermost skin layers, such as the stratum corneum, to the inner skin layers.

Increasing the hydration of the outermost layers of skin decreases the impact of air pockets on the incident signal. Hydration, thus, results in a greater percentage of the incident photons reaching analyte rich skin volume. Hydration is achieved through a variety of means, such as occlusion, direct water contact, and increasing localized perfusion.

A preferred means of the optional hydration step is hydration by occlusive blockage of trans-epidermal water loss. This blockage ensures a steady state hydration as water diffusing from interior tissue is trapped in the stratum corneum. Attainment of high hydration levels reduces the water concentration gradient that provides the driving force for this trans-epidermal water movement. In a first case, an occlusive plug fits snugly into a guide aperture during periods between measurements, acting to insulate the tissue in the guide aperture from trans-epidermal water loss and the environmental effects of temperature and humidity that are known to influence the stratum corneum hydration state. In a second case, an occlusive patch is used, such as wrapping or covering the tissue sample site with a flexible polymer sheet. In a third case, a window or optic is contacted with the sample site to increase the localized skin surface and shallow depth hydration and/or to stabilize the tissue by providing the same tissue displacement as the probe. The optic is continuously, replaceably, or intermittently attached to the sample site. Examples of optics include a window, a longpass filter, and a bandpass filter. In a fourth case, hydration means include a material that provides a hydration barrier, thus promoting the full and stable hydration of the stratum corneum. Typically, the occlusion means use a hydrophobic material, such as cellophane. In general, optional perfusion enhancement or regulation means are used to increased precision and accuracy in analyte property estimation by the removal or reduction of dry or pocketed skin at the sampling site.

Other solutions to the problem of maintaining hydration of the stratum corneum, consistent with the spirit and scope of the invention are possible, including, but no limited to:
   a vapor barrier or semi-permeable membrane (for example, GORE-TEX, manufactured by W. L. Gore and Associates of Newark, Del. as the mount) in the form of a wrap or a patch configured to cover the site target for measurement. In this latter embodiment the patch is affixed to the tissue site through an adhesive or other attachment mechanism such as a strap or a wrap;
   non-occlusive mechanisms for hydration of the stratum corneum may also be used, including:
      an application of water that is pneumatically driven into the skin;
      ultrasound energy applications to accelerate passive occlusion;
      topical application of skin toners and other water/solute mixtures such as alpha hydroxy acid solutions that serve to drive water and solute into the dry outer skin layer; and
      topical analgesic formulations that enhance and/or stimulate local circulation at the measurement site leading to an improvement in surface hydration.

Coupling Fluid

A coupling fluid is optionally used with the targeting and/or measuring system. An optical coupling fluid with a refractive index between that of the skin surface and the contacting medium is preferably used. However, a coupling fluid need not be a refractive index matching fluid in order to increase light throughput. For example, in the case of a high refractive index material, such as a lens, optical window, or filter, coming into contact with skin via a coupling fluid, the coupling fluid need not have a refractive index between that of skin and the optic to be beneficial. For example, the percentage of incident photons passing through a silicon lens into skin is increased even with use of a coupling fluid that does not have a refractive index between that of silicon and skin. For example, FC-40 (a fluorocarbon) has an index of refraction of 1.290 that is not between that of skin, 1.38, and silicon, approximately 3.45. However, the FC-40 still increases incident photon penetration by displacement of air. For example, for coupling silicon and skin FC-40 is not an index-matching medium, optical coupling fluid, or refractive-index matching coupling fluid; however, FC-40 is a coupling fluid that aids in light coupling by displacing the air.

Preferable coupling fluids are minimally inactive or inactive in terms of absorbance in the spectral region of interest. For example, in the near-infrared fluorocarbons, such as FC-40, have minimal absorbance and are good coupling fluids. In addition, coupling the relatively smooth surface of an optical probe with the irregular skin surface leads to air gaps between the two surfaces. The air gaps create an interface between the two surfaces that adversely affects the measurement during optical sampling of tissue due to refractive index considerations as described, supra. A coupling medium is used to fill these air gaps. Preferably, for an application, such as noninvasive glucose estimation, the coupling fluid:

is spectrally inactive;

is non-irritating;

is nontoxic;

has low viscosity for good surface coverage properties;

has poor solvent properties with respect to leaching fatty acids and oils from the skin upon repeated application; and is thermally compatible with the measurement system.

In one example, a coupling fluid is preheated to between about 90 and 95° F., preferably about 92° F. Preheating the coupling fluid minimizes changes to the surface temperature of the contacted site, thus minimizing spectral changes observed from the sampled tissue.

The coupling fluid is optionally delivered in a manual, semi-automated, or automated fashion.

Mount

In the preferred embodiment of the invention, neither the targeting system nor the measurement system use a mount in the sampling process. However, a guide or optionally a mount is optionally used with one or both of the targeting system and measurement system.

A key characteristic of an optional adaptive mount is achievement of highly repeatable sampling by limiting stress and strain on and/or about the median targeted tissue measurement site. To achieve this, the mount adapts to physical changes in the sample. An additional benefit of the adaptive mount is that it optionally provides a means for locally registering the location of the targeted tissue volume with respect to the optical probe and/or tip of a sample module, such that a narrow range of tissue volumes are sampled by the optical system. Local registration refers to controlling the position of the optical probe relative to a target location on the tissue. The adaptive mount allows flexibility in terms of the exact position of the tissue that is sampled. This allows the sample to undergo stress, expand, contract, and/or twist and the mount adapts to the new state of the sample by mounting a sample probe to a slightly new position in terms of x-position and y-position, described infra. Means for registering the mount and the optical probe are optionally mechanical, optical, electrical, and/or magnetic.

Figure 7:
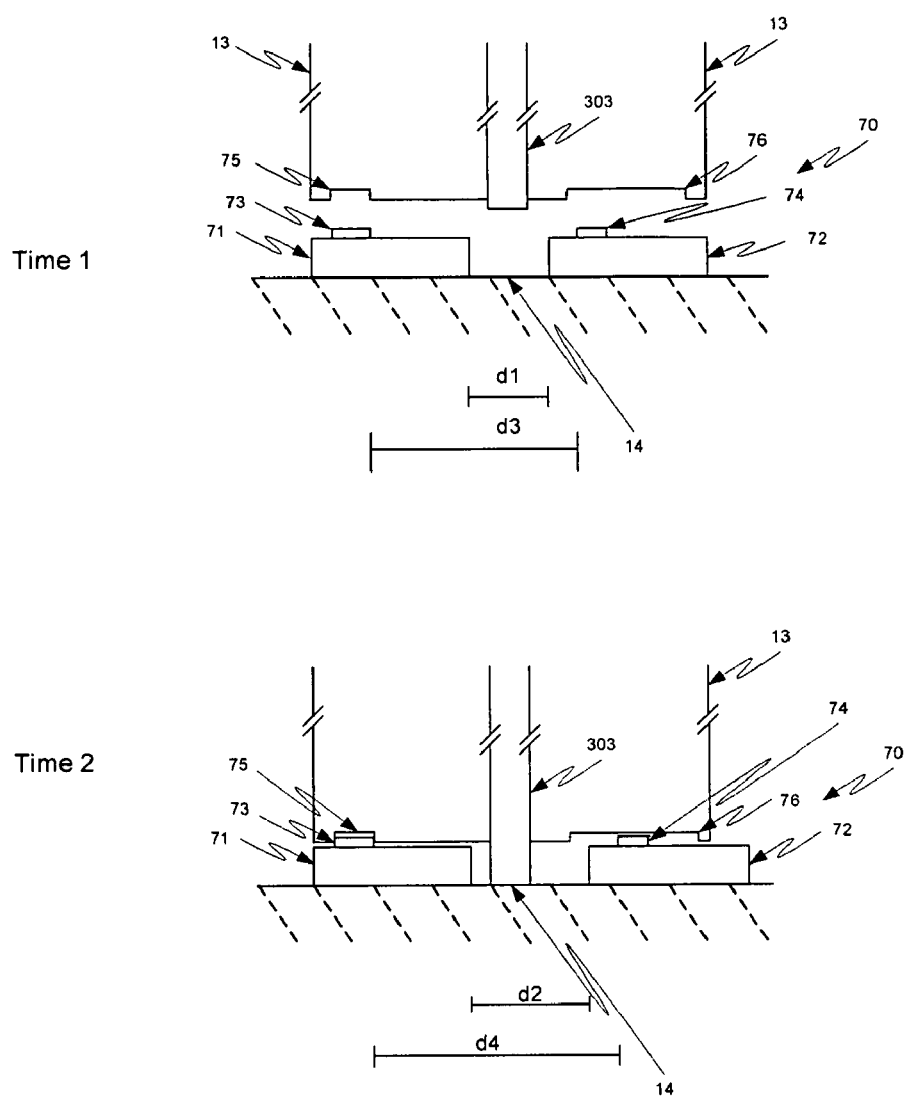
FIG. 7 illustrates an embodiment of a dynamic mount according to the invention.

An example of an adaptive mount is presented that increases precision and accuracy of noninvasive sampling, which results in increased sensitivity, precision, and accuracy of subsequent analyte property estimation derived from the sampling. The adaptive mount is placed onto the skin of a person. Between uses, opposing ends of the adaptive mount move relative to each other as the skin tissue state changes. During use, the adaptive mount is designed to minimize skin deformation during placement of a sample probe of an analyzer or during placement of a plug. In one example, the adaptive mount samples a dynamic x-, y-position at or about a central sample site. In another example, the adaptive mount is deformable, which distributes applied forces during sample about the sample site. In these examples, at least one axis of the sample probe is allowed to float relative to a fixed x,y-point that defines a given sample site. Referring now to FIG. 7, an example of an adaptive mount with freedom of motion along the x-axis is presented at two moments in time. At time 1, the tissue 14 has a distance, d1, between a first alignment piece 71 and a second alignment piece 72. The two alignment pieces 71, 72 have corresponding means for registration 73, 74. The two registration pieces 73, 74 pieces are integral to the alignment pieces 71, 72 or are separate pieces.

At time 1, the two registration pieces 73, 74 have a distance, d3, between them. In this case, the registration pieces protrude from the alignment pieces. A portion of a sample module 13 is represented near the tissue 14. Registration pieces 75, 76 correspond to the registration pieces on the mount 73, 74, respectively. In this case, registration piece 75 acts as one-half of a lock and key element corresponding to the second half of a lock and key element 73. A sample probe 303 is situated at a given x-, y-position relative to the tissue 14.

At time 2, the tissue 14 has changed state. In the state pictured, the tissue has elongated resulting in the distance between the first and second alignment pieces 71, 72 to expand in distance from d1 to d2. The corresponding distance between the first and second registration pieces 73, 74 has similarly expanded in distance from d3 to d4. In the example, the sample module 13 includes one registration piece 75 that couples with a corresponding registration piece 71 on the mount 70. A second registration piece 76 on the sample module 13 has freedom of movement in at least one-dimension relative to the alignment piece 72 and/or registration piece 74. The tip of the sample probe 303 mounts to a slightly different x-, y-position of the tissue 14 as the tissue state changes in a manner that effects the tissue size, shape, and/or torque. This results in at least a portion of the sample module 13 and/or sample probe 303 to mount on the mount 70 via one or more alignment pieces and/or one or more registration pieces with minimal deformation or strain on the tissue 14. The mounting of the sample probe 303 to the mount 70 with minimal strain results in noninvasive spectra with fewer spectral interferences and hence corresponding analyte property estimation is more precise and accurate. Optionally, the sample probe 303 is movable along the z-axis, so that the tip of the sample probe results in minimal stress on the sample tissue volume. In the pictured instance, the sample probe is shown as extended to the tissue 14 at time 2. A movable z-axis sample probe is optionally used with this system, supra.

Similarly, the variable placement of the sample probe relative to the tissue is performed along the y-axis or through a combination of x- and y-axis. For example, the alignment piece 72 optionally contains means, such as groove along the y-axis for y-axis freedom of movement or a slide, such as a planar surface, for x- and y-axis freedom of movement.

Pathlength/Depth of Penetration

Optionally, one or both of the targeting and measuring systems target a depth of skin tissue. In a first example, the measuring system is adjusted to a pathlength or depth in the absence of a targeting system. In a second example, the targeting system targets a depth. In a third example, a targeted depth is the cutaneous layer of skin tissue. In the case of a hydrophilic analyte, such as glucose, the depth targeting of photons into a perfused or aqueous rich layer increases the sampling photon density in the analyte rich region and minimizes photon density in the adipose layer.

The depth of penetration and pathlength of collected photons is dependent upon the tissue state and properties of the tissue, such as scattering and absorbance. Generally, lower scattering results in deeper maximum photon depth of penetration. As absorption increases, the photons traveling deeper have a smaller probability of returning to the incident surface. Thus, effective depth of penetration of collected photons is dependent upon both parameters. In addition, scattering and depth of penetration affect the optical pathlength. Generally, photons collected at an incident surface with deeper penetration and/or greater radial diffusion have, on average, longer pathlengths. Since scattering and absorbance are wavelength dependent, the average depth of penetration and pathlength are also wavelength dependent.

The depth of penetration and pathlength of collected photons is also dependent upon the analyzer optical configuration. In one example, a cutaneous sampling optical probe limits the radial distance between incident photons directed at the skin and the collected photons coming from the skin. Optional radial range limits include a minimum range, a maximum range, or both a minimum and maximum range. For example, very short pathlengths are effectively blocked using a spacer between a region of incident photons contacting the skin and a region where photons are collected from the skin. Example include a thin or thick blocker, such as a blade, a gap, and an optically opaque sheath, such as a fiber optic coating. This spacer is optionally used to block specular light in embodiments where the optics do not come into close proximity with the skin. A maximum range is defined by the far reaches of the incident illumination area and collection area.

Figure 8:
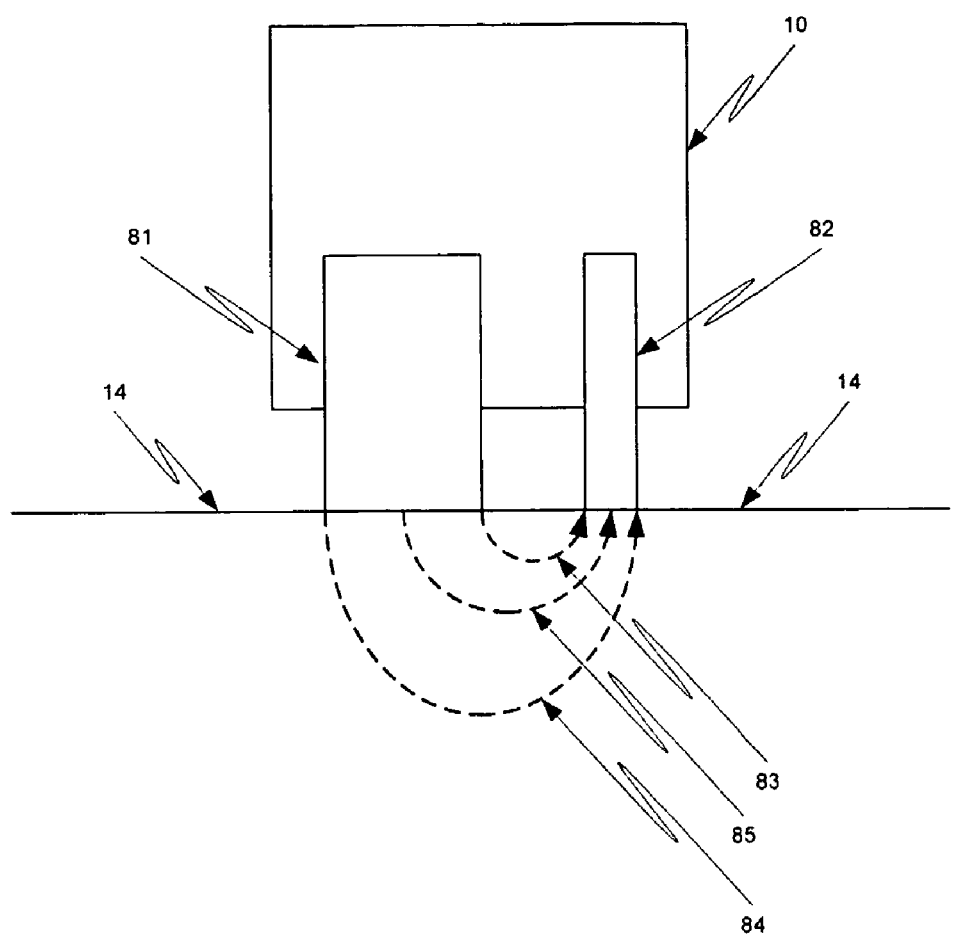
FIG. 8 illustrates control of depth of penetration and pathlength according to the invention.

Referring now to FIG. 8, an example of an analyzer 10 with a given pathlength and/or optical depth is provided. An illumination probe 81 delivers photons to the tissue sample 14. A collection probe 82 collects light emerging from a collection area. On average, short depths and short photonic pathlengths in tissue result from photons with the shortest radial distance to travel 83. Photons having the longest radial distance to travel between the illumination area and collection area typically have the largest average depth of penetration and pathlength 84. Intermediate radial distances typically result in intermediate depths of penetration and pathlength 85. The average pathlength and depth of penetration is increased by moving the illumination area further from the collection area. Similarly, smaller pathlengths and shallower penetration depths are achieved by moving the illumination area closer to the collection area. By controlling the illumination area(s), collection area(s) and radial distance(s) between the areas, the sample volume, optical depth, and pathlength are controlled. Controlled distance between the illumination area and detection area is optionally static, dynamic, or adjustable to a person or to a tissue state.

In another example of pathlength and/or depth of penetration control, a fiber bundle or a plurality of bundlets are used. The spacing between the illumination and collection fibers of each bundlet, and the spacing between bundlets is optimized to minimize sampling of the adipose subcutaneous layer and to maximize collection of light that has been backscattered from the cutaneous layer. This example optimizes penetration depth by limiting the range of distances between illumination fibers and detection fibers. By minimizing sampling of the adipose layer, interference contributed by the fat band is greatly reduced in the sample spectrum, thereby increasing the signal-to-noise ratio for the target analyte. The provision of multiple bundlets also minimizes interference in the sample spectrum due to placement errors.

The pathlength and depth of penetration of photons in a tissue sample are optionally controlled through others means. In a first example, mechanical and/or optical means are used to change the illumination area lit by a source and/or the collection area observed by a detector. As described, infra, this changes the average pathlength and depth of penetration. For example, a changing blocker thickness or iris diameter are used to expand or contract the illumination and/or detector area. For the exemplar case of an iris, the iris is optionally mechanically opened and shut or is optically expanded or contracted. For example, a liquid crystal is used to black out or make opaque regions of the illumination and/or collection area. In a second example, a reflector shape is changed with time causing the illumination area lit or detection area observed to expand or contract. For example, a shape of a back reflector behind a source is changed to create larger or smaller illumination areas, such as a circle with a different diameter, on the sample. In a third example, the incident angle of the photons is changed. This alters the initial angle of the photons entering the sample. This initial angle operates in conjunction with scattering and absorbance to result in an altered average depth of penetration and/or pathlength of the photons into the sample. In a fourth example, fiber rings are used for illumination and/or collection. In a fifth example, a wheel is rotated in the optical train prior to the sample. The wheel has transmissive, semi-transmissive, or opaque regions as a function of wavelength and/or position. In the case of a wheel with open sections and closed sections that is spun, the average pathlength is varied. The wheel is spun in a light source that the average distance of the open areas varies as a function of time. Preferably a second wheel is used so that only the open areas of interest are viewed at a given time by the detecting system. This allows a detector to see different depths of the same sample through time or for an array to see different depths and pathlengths of a sample at a single point in time or through time. In a sixth example, part of an analyzer is redirected to a new sample site. For example, part of a sample probe is used to aim the sample probe to a new sampled area.

Optionally, probed tissue pathlength is controlled by tailoring the distance distribution between optical illuminator conduits and the detector conduit using a digital mirror array. In this embodiment, light passes from a multiplicity of illuminator conduits into the skin and from the skin into a centrally located detector conduit. Source light is separated into different optical channels defined by individual fibers in a short fiber bundle into which the source light is focused. Preferably, a digital mirror array, or DLP chip, is used to separate the source light into individual fibers or a few fibers in an illumination bundle. Focused light is reflected off of the mirror array onto the fiber optic and individual mirror angles on the chip are controlled to reflect full, partial, or no intensity onto individual illumination fibers. Since each fiber represents an element in the source/detector distance distribution, manipulation of the reflected light allows for tailoring or even optimization of the light launch distribution into the tissue. Such flexibility allows for pathlength correction of the measured diffuse reflectance signal.

Data Processing

The analyzer preferably includes a data processing module, which is used in generation of an analyte property using signal generated from the targeting system and/or the measuring system. The data processing module preferably uses data preprocessing and/or data processing techniques in combination with the invention. Generally, a method and apparatus correct for tissue related interference for the purpose of calibration and measurement of biological parameters noninvasively. The method is described in terms of outlier identification, filtering, spectral correction, and baseline subtraction steps that, when used together, enable the noninvasive measurement of a biological parameter, such as glucose concentration.

Figure 9:
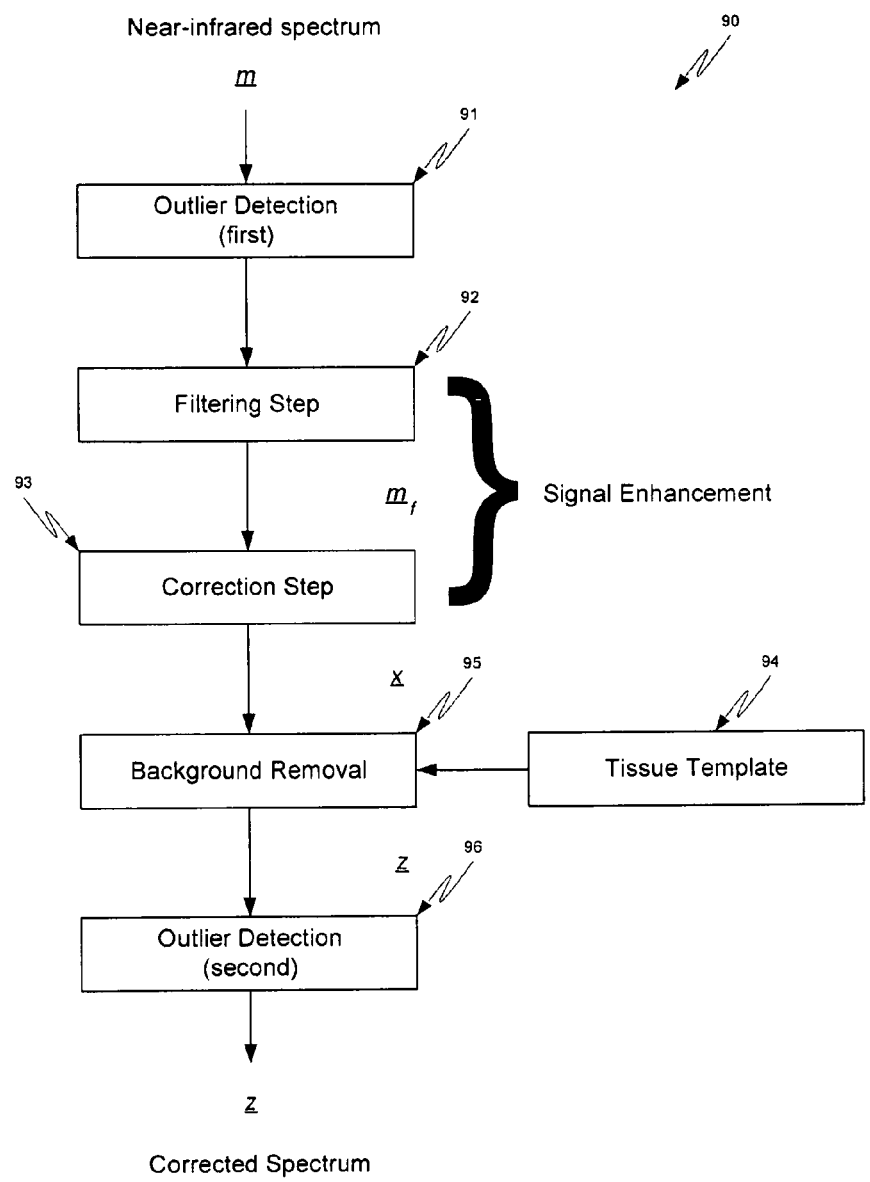
FIG. 9 provides a block diagram of processing spectra according to the invention.

Referring now to FIG. 9, a block diagram summarizing processing 90 of the near-infrared signal is presented. The steps are all preferably used in the order illustrated. Alternatively, one or more steps are omitted and/or the steps are performed in an alternative order. The method optionally includes both gross 91 and detailed 96 methods for detecting outliers or anomalous measurements that are incompatible with the processing methods or are the result of sampling or instrument errors. Spectral correction, involving the steps of filtering 92 and/or correction 93, is applied to compensate for noise and interference and to adjust a spectrum according to local or minor changes in the optical properties of the tissue sample. The step of background removal 95 reduces variation in the measurement, such as variation associated with sample-site differences, dynamic tissue changes, and subject-to-subject variation. An optional tissue template 94 is used to remove background 95. Examples of a tissue template include a spectrum of the subject being measured, a basis set, or a computed spectrum of a cluster of spectral data.

A background removal step preferably follows the steps defined above and uses a spectral background or tissue template. For example, the background removal step performed by calculating the difference between the estimated spectral background or tissue template and x through $$z = x - (cx_t + d) \quad (3)$$

where $x_t$ is the estimated background or tissue template, c and d are slope and intercept adjustments to the tissue template. Direct subtraction is just one form of background removal. The spectrally corrected signal, z, is used for calibration development or measurement of a target analyte. The background is estimated on the basis of an optimal selection of spectrally corrected measurements collected prior to the measurement, m. The variables c and d are preferably determined on the basis of features related to the dynamic variation of the tissue.

In one embodiment, $x_1$ is a spectrally corrected spectral measurement collected on tissue at the beginning of a measurement period. The measurement period is defined as a time period during which the state of the tissue sample is uniform. Further detail on basis sets is provided in U.S. Pat. No. 6,115,673, which is incorporated herein in its entirety by this reference thereto.

In a first example, the background removal step uses a basis set of spectral interferences to remove the signals that are specific to a given sampled tissue volume, such as the background. The optical estimate of the background are performed subsequent to the removal of noise and the correction of the spectrum.

In a second example, the following steps are performed to process the spectra:
  averaging spectra;
  correcting dead pixels;
  calculating absorbance;
  performing x-axis standardization;
  uniformly re-sampling the spectrum to standardize the x-axis;
  performing a first (gross) outlier detection;
  correcting the spectrum;
  performing a wavelength selection;
  removing interference; and
  performing a second (fine) outlier detection The order of the steps is optionally varied. For example, the wavelength selection step is optionally performed out of sequence, such as after the second outlier detection or before any of the earlier steps. In addition, not all steps are required. For example, correcting dead pixels is not appropriate to some analyzers. As a second example, conversion to absorbance is not always required, nor are other steps.

Intelligent System

An optional intelligent system for measuring blood analyte properties is used in combination with the invention. The system operates on near-infrared absorbance spectra of in-vivo skin tissue. The architecture employs a pattern classification engine to adapt the calibration to the structural properties and physiological state of the patient as manifested in the absorbance spectrum. Optionally, a priori information about the primary sources of sample variability are used to establish general categories of patients. Application of calibration schemes specific to the various categories results in improved calibration and prediction.

Two classification methods are optionally used. The first assumes the classes are mutually exclusive and applies specific calibration models to the various patient categories. The second method uses fuzzy set theory to develop calibration models and blood analyte predictions. In the second, each calibration sample has the opportunity to influence more than one calibration model according to its class membership. Similarly, the predictions from more than one calibration are combined through defuzzification to produce the final blood analyte property estimation.

Based on the two classification rules, two implementations of the intelligent measurement system are detailed for the noninvasive estimation of the concentration of blood glucose. The first uses spectral features related to gross tissue properties to determine which of several prediction models is the most likely to produce an accurate blood glucose estimation. The extracted features are representative of the actual tissue volume irradiated. The second employs a fuzzy classification system to assign a degree of membership in each of several classes to the spectral measurement. The membership is used to aggregate the predictions of calibrations associated with each class to produce the final blood glucose prediction. Optionally, the membership strategy is employed during calibration in modified form of weighted principal components regression to produce calibrations from the entire population of samples. Additional description of an intelligent system is provided in U.S. Pat. No. 6,280,381, which is incorporated herein in its entirety by this reference thereto.

Those skilled in the art will recognize that the present invention may be manifested in a variety of forms other than the specific embodiments described and contemplated herein. Departures in form and detail may be made without departing from the spirit and scope of the present invention. Accordingly, the invention should only be limited by the Claims included below.

The invention claimed is:

1. An apparatus for noninvasive determination of an analyte property of a tissue sample, comprising:
   a targeting system configured to perform a measurement related to the tissue sample, wherein said targeting system generates a first signal, wherein said first signal comprises any of:
   a capacitance sensor signal;
   and
   a fluorescence signal;
   a measuring system, wherein said measuring system generates a second signal optically representative of the tissue;
   a controller, wherein said first signal from said targeting system is used by said controller during positioning of said measuring system relative to the tissue sample; and
   a data processing module, wherein said module generates said analyte property using said second signal.

2. The apparatus of claim 1, wherein said first signal is a fluorescence signal and said targeting system and said measuring system commonly use at least one optic.

3. The apparatus of claim 1, wherein said first signal is a fluorescence signal and said targeting system comprises a functional first set of optics, wherein said measuring system comprises a second set of functional optics, and wherein none of said first set of optics is in common with said second set of optics.

4. The apparatus of claim 1, wherein at least a portion of said targeting system comprises a physical location within a housing containing at least a portion of said measuring system.

5. The apparatus of claim 1, wherein said targeting system further comprises a first housing, wherein said measuring system further comprises a second housing, and wherein said first housing is physically separated from said second housing.

6. An apparatus for noninvasive determination of an analyte property of a sample site of a tissue, comprising:
   an analyzer, comprising:
      a targeting system configured to perform a measurement related to the tissue sample, wherein said targeting system generates a first signal, wherein said first signal comprises any of:
         a capacitance sensor signal; and
         a fluorescence signal;
      a measuring system,
         wherein said first signal is used in dynamically positioning said measuring system relative to the sample site; and
         wherein said measuring system generates a second signal optically representative of the tissue; and
      a data processing module, wherein said module generates said analyte property using said second signal.

7. The apparatus of claim 6, wherein said first signal is a capacitance sensor signal and comprises a representation of a distance between said measuring system and the sample.

8. The apparatus of claim 6, wherein said first signal is a fluorescence signal and represents position of said targeting system relative to a non-tissue target, wherein said non-tissue target is imbedded within, positioned on, or attached to the tissue.

9. The apparatus of claim 6, wherein said first signal comprises a representation of any of:
   a biological feature of the tissue sample;
   a chemical feature of the tissue sample;
   a physical feature;
   a natural component of the tissue sample;
   a dermis thickness;
   a subcutaneous feature.

10. The apparatus of claim 6, further comprising a controller used during movement of any of:
    said measuring system;
    said targeting system;
    an actuator; and
    the tissue sample.

11. The apparatus of claim 6, wherein said measuring system comprises a base module in a first housing and a sample module in a second housing, wherein said first housing and said second housing are physically separated and communicatively linked.

12. The apparatus of claim 6, wherein said measuring system further comprises:
    a first optic positioned in an optical train after said source; and
    a second optic in said optical train configured to be between said first optic and the sample,
    wherein said first optic removes a least one heat generating wavelength outside of a range of wavelengths used by said data processing module, and
    wherein position of said second optic is configured to be proximate the tissue sample.

13. The apparatus of claim 6, wherein said targeting system further comprises a capacitance sensor used to generate said first signal.

14. The apparatus of claim 13, wherein said first signal is a capacitance sensor signal and indicates any of:
    distance between a sample probe tip of said measuring system and the sample site of the tissue; and
    tilt of a sample probe of said measuring system relative to the sample site of the tissue.

15. A method for noninvasively determining an analyte property of a sample site of a tissue, comprising:
    generating a targeting signal related to the tissue using a targeting system, wherein said targeting system comprises a portion of said analyzer, wherein said targeting signal comprises any of:
    a capacitance sensor signal; and
    a fluorescence signal;
    using said targeting signal in positioning a measuring system relative to the sample site;
    generating a noninvasive signal using said measuring system, wherein said noninvasive signal optically represents the tissue; and
    processing said noninvasive signal to yield said analyte property.

16. The method of claim 15, further comprising the step of:
    dynamically generating said noninvasive signal during said step of positioning said measuring system.

17. The method of claim 15, wherein said step of generating said noninvasive signal comprises spectral data collection during and/or after said step of positioning said measuring system.

18. The method of claim 15, wherein said step of positioning said measuring system comprises movement of at least a portion of said measuring system in space through any of:

an x-axis;
a y-axis;
a z-axis;
rotation; and
tilt,
wherein said x-axis is defined along the length of a body part; said y-axis is defined across the body part; said z-axis is defined as orthogonal to the plane defined by the x- and y-axes; said tilt is an off z-axis alignment of longitudinal orientation a sample probe of the measuring system, wherein longitudinal orientation extends from a tip of said sample probe tip interfacing with a sample site to the opposite end of said sample probe.

19. The method of claim 15, wherein said step of generating said noninvasive signal comprises spectral data collection during a time period comprising any of:
   no contact of said measuring system with the sample;
   proximate contact of said measuring system with the sample;
   contact of said measuring system with the sample; and
   displacement of at least a portion of the sample by said measuring system.

20. The method of claim 15, further comprising the step of:
   using said second signal in determination of stress/strain of the tissue.

21. The method of claim 15, wherein said targeting signal targets a depth of the tissue.

22. A method for noninvasively determining an analyte property of a sample site of a tissue, comprising:
   generating a targeting signal with a capacitance signal sensor in a targeting system, wherein said targeting system comprises a portion of an analyzer;
   using said targeting signal in positioning a measuring system relative to the sample site, wherein said step of positioning said measuring system comprises tilt movement of at least a portion of said measuring system in space,
   wherein an x-axis is defined along the length of a body part; a y-axis is defined across the body part; a z-axis is defined as orthogonal to the plane defined by the x- and y-axes; and said tilt is a rotation about said x-axis and/or said y-axis;
   generating a noninvasive signal using said measuring system, wherein said noninvasive signal optically represents the tissue; and
   processing said noninvasive signal to yield said analyte property.

* * * * *